US012358997B1

(12) United States Patent
Duerr et al.

(10) Patent No.: US 12,358,997 B1
(45) Date of Patent: *Jul. 15, 2025

(54) BISPECIFIC ANTI-HUMAN A-BETA/ANTI-HUMAN TRANSFERRIN RECEPTOR ANTIBODIES

(71) Applicant: HOFFMANN-LA ROCHE INC., Little Falls, NJ (US)

(72) Inventors: Harald Duerr, Starnberg (DE); Sebastian Fenn, Achmuehle/Eurasburg (DE); Ulrich Goepfert, Penzberg (DE); Sabine Imhof-Jung, Planegg (DE); Christian Klein, Bonstetten (CH); Laurent Lariviere, Munich (DE); Michael Molhoj, Munich (DE); Joerg Thomas Regula, Munich (DE); Petra Rueger, Penzberg (DE); Wolfgang Schaefer, Mannheim (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/093,136

(22) Filed: Mar. 27, 2025

Related U.S. Application Data

(60) Continuation of application No. 18/132,486, filed on Apr. 10, 2023, which is a continuation of application No. 17/130,477, filed on Dec. 22, 2020, now Pat. No. 11,787,868, which is a division of application No. 15/941,655, filed on Mar. 30, 2018, now Pat. No. 10,941,205, which is a continuation of application No. PCT/EP2016/073411, filed on Sep. 30, 2016.

(30) Foreign Application Priority Data

Oct. 2, 2015 (EP) ..................... 15188064

(51) Int. Cl.
*A61K 39/00* (2006.01)
*A61K 38/40* (2006.01)
*A61K 39/395* (2006.01)
*A61P 25/28* (2006.01)
*C07K 16/00* (2006.01)
*C07K 16/18* (2006.01)
*C07K 16/28* (2006.01)
*C07K 16/46* (2006.01)

(52) U.S. Cl.
CPC .......... *C07K 16/2881* (2013.01); *A61P 25/28* (2018.01); *C07K 16/18* (2013.01); *C07K 16/468* (2013.01); *A61K 2039/505* (2013.01); *C07K 2317/31* (2013.01); *C07K 2317/51* (2013.01); *C07K 2317/515* (2013.01); *C07K 2317/52* (2013.01); *C07K 2317/522* (2013.01); *C07K 2317/55* (2013.01); *C07K 2317/56* (2013.01); *C07K 2317/64* (2013.01)

(58) Field of Classification Search
CPC ............ C07K 2317/31; C07K 2317/55; C07K 16/18; C07K 2317/565; C07K 2317/24; C07K 2317/56; C07K 14/79; C07K 2317/515; C07K 2317/54; C07K 2317/66; C07K 16/28; A61K 2039/505; A61K 47/6849; A61K 39/0007; A61K 39/395; A61K 38/177; A61K 38/40; A61P 25/28; A61P 25/00; G01N 33/6896; G01N 2800/2821; G01N 2333/4709; G01N 2800/28
See application file for complete search history.

(56) References Cited

U.S. PATENT DOCUMENTS

| | | |
|---|---|---|
| 3,773,919 A | 11/1973 | Boswell et al. |
| 4,120,649 A | 10/1978 | Schechter et al. |
| 4,665,077 A | 5/1987 | Stringfellow et al. |
| 4,666,829 A | 5/1987 | Glenner et al. |
| 4,737,456 A | 4/1988 | Weng et al. |
| 4,816,567 A | 3/1989 | Cabilly et al. |
| 4,861,579 A | 8/1989 | Meyer, Jr. et al. |
| 4,892,538 A | 1/1990 | Aebischer et al. |
| 5,114,721 A | 5/1992 | Cohen et al. |
| 5,154,924 A | 10/1992 | Friden |
| 5,195,317 A | 3/1993 | Nobue et al. |
| 5,208,020 A | 5/1993 | Chari et al. |
| 5,231,000 A | 7/1993 | Majocha et al. |
| 5,283,187 A | 2/1994 | Aebischer et al. |
| 5,416,064 A | 5/1995 | Chari et al. |
| 5,427,927 A | 6/1995 | Meyer et al. |
| 5,500,362 A | 3/1996 | Robinson et al. |
| 5,595,721 A | 1/1997 | Kaminski et al. |
| 5,624,821 A | 4/1997 | Winter et al. |
| 5,635,483 A | 6/1997 | Pettit et al. |
| 5,648,237 A | 7/1997 | Carter et al. |

(Continued)

FOREIGN PATENT DOCUMENTS

| | | |
|---|---|---|
| CN | 101245107 A | 8/2008 |
| EP | 0332865 A2 | 9/1989 |

(Continued)

OTHER PUBLICATIONS

Schaefer et al., PNAS, 2011; 108:11887-11192.*

(Continued)

*Primary Examiner* — Chang-Yu Wang
(74) *Attorney, Agent, or Firm* — MORRISON & FOERSTER LLP

(57) ABSTRACT

Herein are provided bispecific anti-human A-beta/human transferrin receptor antibodies and methods of using the same.

2 Claims, No Drawings

Specification includes a Sequence Listing.

(56) References Cited

U.S. PATENT DOCUMENTS

| | | |
|---|---|---|
| 5,648,260 A | 7/1997 | Winter et al. |
| 5,677,180 A | 10/1997 | Robinson et al. |
| 5,688,651 A | 11/1997 | Solomon et al. |
| 5,712,374 A | 1/1998 | Kunstmann et al. |
| 5,714,586 A | 2/1998 | Kunstmann et al. |
| 5,721,108 A | 2/1998 | Robinson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,776,456 A | 7/1998 | Anderson et al. |
| 5,780,588 A | 7/1998 | Pettit et al. |
| 5,789,199 A | 8/1998 | Joly et al. |
| 5,821,337 A | 10/1998 | Carter et al. |
| 5,840,523 A | 11/1998 | Simmons et al. |
| 5,843,398 A | 12/1998 | Kaminski et al. |
| 5,843,439 A | 12/1998 | Anderson et al. |
| 5,849,898 A | 12/1998 | Seed et al. |
| 5,877,296 A | 3/1999 | Hamann et al. |
| 5,955,317 A | 9/1999 | Suzuki et al. |
| 5,959,177 A | 9/1999 | Hein et al. |
| 6,008,326 A | 12/1999 | Loosmore et al. |
| 6,015,542 A | 1/2000 | Kaminski et al. |
| 6,015,555 A | 1/2000 | Friden |
| 6,040,498 A | 3/2000 | Stomp et al. |
| 6,066,652 A | 5/2000 | Zenner et al. |
| 6,075,181 A | 6/2000 | Kucherlapati et al. |
| 6,083,747 A | 7/2000 | Wong et al. |
| 6,090,365 A | 7/2000 | Kaminski et al. |
| 6,120,767 A | 9/2000 | Robinson et al. |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,224,866 B1 | 5/2001 | Barbera-Guillem |
| 6,242,195 B1 | 6/2001 | Idusogie et al. |
| 6,267,958 B1 | 7/2001 | Andya et al. |
| 6,287,537 B1 | 9/2001 | Kaminski et al. |
| 6,306,393 B1 | 10/2001 | Goldenberg et al. |
| 6,368,596 B1 | 4/2002 | Ghetie et al. |
| 6,399,061 B1 | 6/2002 | Anderson et al. |
| 6,410,391 B1 | 6/2002 | Zelsacher |
| 6,417,429 B1 | 7/2002 | Hein et al. |
| 6,420,548 B1 | 7/2002 | Vezina et al. |
| 6,455,043 B1 | 9/2002 | Grillo-Lopez |
| 6,528,624 B1 | 3/2003 | Idusogie et al. |
| 6,538,124 B1 | 3/2003 | Idusogie et al. |
| 6,565,827 B1 | 5/2003 | Kaminski et al. |
| 6,602,684 B1 | 8/2003 | Umana et al. |
| 6,630,579 B2 | 10/2003 | Chari et al. |
| 6,652,852 B1 | 11/2003 | Robinson et al. |
| 6,682,734 B1 | 1/2004 | Anderso |
| 6,737,056 B1 | 5/2004 | Presta et al. |
| 6,982,321 B2 | 1/2006 | Winter et al. |
| 7,041,870 B2 | 5/2006 | Tomizuka et al. |
| 7,087,409 B2 | 8/2006 | Barbas et al. |
| 7,125,978 B1 | 10/2006 | Vezina et al. |
| 7,189,826 B2 | 3/2007 | Rodman |
| 7,332,581 B2 | 2/2008 | Presta et al. |
| 7,371,826 B2 | 5/2008 | Presta et al. |
| 7,498,298 B2 | 3/2009 | Doronina et al. |
| 7,521,541 B2 | 4/2009 | Eigenbrot et al. |
| 7,527,791 B2 | 5/2009 | Adams et al. |
| 7,687,061 B2 | 3/2010 | Hanai et al. |
| 7,794,719 B2 | 9/2010 | Bardroff et al. |
| 8,187,594 B2 | 5/2012 | Mather et al. |
| 8,216,577 B2 | 7/2012 | Bardroff et al. |
| 8,313,913 B2 | 11/2012 | Nakamura et al. |
| 8,329,886 B2 | 12/2012 | Bardroff et al. |
| 8,883,980 B2 | 11/2014 | Umana et al. |
| 8,906,370 B2 | 12/2014 | Loetscher et al. |
| 8,945,867 B2 | 2/2015 | Ogawa et al. |
| 9,272,031 B2 | 3/2016 | Loetscher et al. |
| 9,598,496 B2 | 3/2017 | Kurosawa et al. |
| 9,708,406 B2 | 7/2017 | Zhang et al. |
| 9,714,292 B2 | 7/2017 | Auer et al. |
| 10,323,089 B2 | 6/2019 | Dengl et al. |
| 10,323,099 B2 | 6/2019 | Bruenker et al. |
| 10,364,292 B2 | 7/2019 | Rueger et al. |
| 10,370,692 B2 | 8/2019 | Kopetzki et al. |
| 10,808,036 B2 | 10/2020 | Zhang et al. |
| 10,941,205 B2 * | 3/2021 | Duerr .................. C07K 16/468 |
| 11,098,338 B2 | 8/2021 | Kopetzki et al. |
| 11,584,793 B2 | 2/2023 | Dengl et al. |
| 11,603,411 B2 | 3/2023 | Duerr et al. |
| 11,787,868 B2 * | 10/2023 | Duerr .................. C07K 16/468 |
| | | 424/136.1 |
| 12,030,952 B2 | 7/2024 | Duerr et al. |
| 12,252,533 B2 | 3/2025 | Dengl et al. |
| 2001/0018041 A1 | 8/2001 | Hanna et al. |
| 2001/0056066 A1 | 12/2001 | Bugelski et al. |
| 2002/0004587 A1 | 1/2002 | Miller et al. |
| 2002/0006404 A1 | 1/2002 | Hanna et al. |
| 2002/0009427 A1 | 1/2002 | Wolin et al. |
| 2002/0009444 A1 | 1/2002 | Grillo-Lopez et al. |
| 2002/0012665 A1 | 1/2002 | Hanna et al. |
| 2002/0025313 A1 | 2/2002 | Micklus et al. |
| 2002/0041847 A1 | 4/2002 | Goldenberg |
| 2002/0058029 A1 | 5/2002 | Hanna et al. |
| 2002/0127652 A1 | 9/2002 | Schambye et al. |
| 2002/0128488 A1 | 9/2002 | Yamakawa et al. |
| 2002/0136719 A1 | 9/2002 | Shenoy et al. |
| 2002/0164328 A1 | 11/2002 | Shinkawa et al. |
| 2002/0197255 A1 | 12/2002 | Anderson et al. |
| 2002/0197256 A1 | 12/2002 | Grewal et al. |
| 2003/0003097 A1 | 1/2003 | Reff et al. |
| 2003/0021781 A1 | 1/2003 | Anderson et al. |
| 2003/0026801 A1 | 2/2003 | Weiner et al. |
| 2003/0082172 A1 | 5/2003 | Anderson et al. |
| 2003/0095963 A1 | 5/2003 | Anderson et al. |
| 2003/0103971 A1 | 6/2003 | Hariharan et al. |
| 2003/0115614 A1 | 6/2003 | Kanda et al. |
| 2003/0133930 A1 | 7/2003 | Goldenberg et al. |
| 2003/0147885 A1 | 8/2003 | Anderson et al. |
| 2003/0148404 A1 | 8/2003 | Michaelson |
| 2003/0157108 A1 | 8/2003 | Presta et al. |
| 2003/0180292 A1 | 9/2003 | Hanna et al. |
| 2003/0185796 A1 | 10/2003 | Wolin et al. |
| 2003/0202972 A1 | 10/2003 | Andya et al. |
| 2003/0219433 A1 | 11/2003 | Hansen et al. |
| 2003/0219818 A1 | 11/2003 | Bohen et al. |
| 2004/0082762 A1 | 4/2004 | Basi et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0131692 A1 | 7/2004 | Kreuter et al. |
| 2004/0132140 A1 | 7/2004 | Satoh et al. |
| 2004/0180417 A1 | 9/2004 | Seidah et al. |
| 2004/0192898 A1 | 9/2004 | Jia et al. |
| 2004/0197324 A1 | 10/2004 | Liu et al. |
| 2004/0204354 A1 | 10/2004 | Nelson et al. |
| 2004/0248197 A1 | 12/2004 | Holtzman et al. |
| 2005/0014934 A1 | 1/2005 | Hinton et al. |
| 2005/0031613 A1 | 2/2005 | Nakamura et al. |
| 2005/0058644 A1 | 3/2005 | Engelman |
| 2005/0123546 A1 | 6/2005 | Umana et al. |
| 2005/0142133 A1 | 6/2005 | Lazar et al. |
| 2005/0147613 A1 | 7/2005 | Raso |
| 2005/0169925 A1 | 8/2005 | Bardroff et al. |
| 2005/0180972 A1 | 8/2005 | Wahl et al. |
| 2005/0260186 A1 | 11/2005 | Bookbinder et al. |
| 2006/0008883 A1 | 1/2006 | Lazar et al. |
| 2006/0104968 A1 | 5/2006 | Bookbinder et al. |
| 2006/0210557 A1 | 9/2006 | Luisi et al. |
| 2006/0251652 A1 | 11/2006 | Watkins et al. |
| 2007/0061900 A1 | 3/2007 | Murphy et al. |
| 2007/0098721 A1 | 5/2007 | Heinz et al. |
| 2007/0134759 A1 | 6/2007 | Nishiya et al. |
| 2008/0167449 A1 | 7/2008 | Lazar et al. |
| 2008/0241884 A1 | 10/2008 | Shitara et al. |
| 2008/0275220 A1 | 11/2008 | Friess et al. |

(56) References Cited

U.S. PATENT DOCUMENTS

| | | |
|---|---|---|
| 2009/0162359 A1 | 6/2009 | Klein et al. |
| 2009/0252724 A1 | 10/2009 | Loetscher et al. |
| 2009/0263491 A1 | 10/2009 | Kreuter et al. |
| 2009/0297436 A1 | 12/2009 | Garcia-Martinez et al. |
| 2009/0297439 A1 | 12/2009 | Comoglio et al. |
| 2010/0016786 A1 | 1/2010 | Drews et al. |
| 2010/0077498 A1 | 3/2010 | Pardridge et al. |
| 2010/0081796 A1 | 4/2010 | Brinkmann et al. |
| 2010/0098693 A1 | 4/2010 | Pardridge et al. |
| 2010/0121036 A1 | 5/2010 | Fischer et al. |
| 2010/0129357 A1 | 5/2010 | Garcia-Martinez et al. |
| 2010/0172907 A1 | 7/2010 | Bardroff et al. |
| 2010/0190247 A1 | 7/2010 | Lazar et al. |
| 2010/0256338 A1 | 10/2010 | Brinkmann et al. |
| 2010/0290985 A1 | 11/2010 | Pardridge et al. |
| 2010/0322934 A1 | 12/2010 | Imhof-Jung et al. |
| 2011/0070225 A1 | 3/2011 | Goldbach et al. |
| 2012/0034160 A1 | 2/2012 | Ghayur et al. |
| 2012/0141484 A1 | 6/2012 | Garcia-Martinez et al. |
| 2012/0171120 A1 | 7/2012 | Dennis et al. |
| 2012/0244577 A1 | 9/2012 | Dixit et al. |
| 2013/0034554 A1 | 2/2013 | Garcia-Martinez et al. |
| 2013/0039925 A1 | 2/2013 | Bansal |
| 2013/0045206 A1 | 2/2013 | Poul et al. |
| 2013/0078249 A1 | 3/2013 | Ast et al. |
| 2013/0090457 A1 | 4/2013 | Cunningham et al. |
| 2013/0136747 A1 | 5/2013 | Bardroff et al. |
| 2013/0177579 A1 | 7/2013 | Lin et al. |
| 2013/0315901 A1 | 11/2013 | Derosier et al. |
| 2014/0114054 A1 | 4/2014 | Kurosawa et al. |
| 2014/0154254 A1 | 6/2014 | Kannan et al. |
| 2014/0212423 A1 | 7/2014 | Hanzatian et al. |
| 2014/0271459 A1 | 9/2014 | Dutzar |
| 2014/0271464 A1 | 9/2014 | Garcia-Martinez et al. |
| 2014/0271661 A1 | 9/2014 | Ye et al. |
| 2015/0030589 A1 | 1/2015 | Goldbach et al. |
| 2015/0110791 A1 | 4/2015 | Zhang et al. |
| 2015/0125446 A1 | 5/2015 | Klein et al. |
| 2015/0132217 A1 | 5/2015 | Chang et al. |
| 2015/0140003 A1 | 5/2015 | Klauza et al. |
| 2015/0196663 A1 | 7/2015 | Shusta et al. |
| 2015/0266947 A1 | 9/2015 | Sierks |
| 2015/0315296 A1 | 11/2015 | Schaefer et al. |
| 2015/0322149 A1 | 11/2015 | Bohrmann et al. |
| 2015/0353639 A1 | 12/2015 | Watts et al. |
| 2016/0145348 A1 | 5/2016 | Stephan |
| 2018/0171012 A1 | 6/2018 | Sonoda et al. |
| 2018/0222992 A1 | 8/2018 | Duerr et al. |
| 2018/0222993 A1 | 8/2018 | Duerr et al. |
| 2018/0282408 A1 | 10/2018 | Dengl et al. |
| 2018/0291110 A1 | 10/2018 | Klein et al. |
| 2019/0276530 A1 | 9/2019 | Bohrmann et al. |
| 2020/0055931 A1 | 2/2020 | Dengl et al. |
| 2020/0071413 A1 | 3/2020 | Rueger et al. |
| 2020/0216553 A1 | 7/2020 | Seeber et al. |
| 2020/0216554 A1 | 7/2020 | Duerr et al. |
| 2021/0087288 A1 | 3/2021 | Zhang et al. |
| 2021/0301030 A1 | 9/2021 | Duerr et al. |
| 2022/0144963 A9 | 5/2022 | Duerr et al. |
| 2022/0306761 A1 | 9/2022 | Duerr et al. |
| 2023/0220071 A1 | 7/2023 | Dengl et al. |
| 2023/0365702 A1* | 11/2023 | Duerr .................... C07K 16/18 |
| 2024/0317879 A1 | 9/2024 | Duerr et al. |
| 2024/0417451 A1* | 12/2024 | Abrantes ............ C07K 16/2881 |

FOREIGN PATENT DOCUMENTS

| | | |
|---|---|---|
| EP | 0307434 B1 | 9/1993 |
| EP | 0683234 A1 | 1/1994 |
| EP | 0425235 B1 | 9/1996 |
| EP | 0330191 B1 | 10/1996 |
| EP | 0340109 B1 | 5/1997 |
| EP | 1125905 A1 | 8/2001 |
| EP | 2343086 A1 | 7/2011 |
| EP | 2668901 A1 | 12/2013 |
| EP | 2708560 A1 | 3/2014 |
| EP | 2787078 A1 | 10/2014 |
| EP | 3315606 A1 | 5/2018 |
| JP | 2017-187722 A | 10/2017 |
| RU | 2439160 C1 | 1/2012 |
| WO | WO 90/08187 A1 | 7/1990 |
| WO | WO 90/11294 A1 | 10/1990 |
| WO | WO 91/001133 A1 | 2/1991 |
| WO | WO 91/03259 A1 | 3/1991 |
| WO | WO 93/10819 A1 | 6/1993 |
| WO | WO 93/21232 A1 | 10/1993 |
| WO | WO 93/25673 A1 | 12/1993 |
| WO | WO 94/11026 A2 | 5/1994 |
| WO | WO 94/29351 A2 | 12/1994 |
| WO | WO 95/015769 A1 | 6/1995 |
| WO | WO 96/07321 A1 | 3/1996 |
| WO | WO 95/03770 A1 | 7/1996 |
| WO | WO 96/020218 A1 | 7/1996 |
| WO | WO 96/025088 A1 | 8/1996 |
| WO | WO 96/39628 A1 | 12/1996 |
| WO | WO 97/04801 A1 | 2/1997 |
| WO | WO 97/008320 A1 | 3/1997 |
| WO | WO 97/30087 A1 | 8/1997 |
| WO | WO 98/56418 A1 | 12/1998 |
| WO | WO 98/58964 A1 | 12/1998 |
| WO | WO 99/22764 A1 | 5/1999 |
| WO | WO 99/27944 A1 | 6/1999 |
| WO | WO 99/051642 A1 | 10/1999 |
| WO | WO 00/09160 A1 | 2/2000 |
| WO | WO 00/23472 A2 | 4/2000 |
| WO | WO 00/27428 A1 | 5/2000 |
| WO | WO 00/27433 A1 | 5/2000 |
| WO | WO 00/42072 A2 | 7/2000 |
| WO | WO 00/44788 A1 | 8/2000 |
| WO | WO 00/61739 A1 | 10/2000 |
| WO | WO 00/61768 A1 | 10/2000 |
| WO | WO 00/64482 A1 | 11/2000 |
| WO | WO 00/67795 A1 | 11/2000 |
| WO | WO 00/67796 A1 | 11/2000 |
| WO | WO 00/72880 A1 | 12/2000 |
| WO | WO 00/74718 A1 | 12/2000 |
| WO | WO 00/76542 A1 | 12/2000 |
| WO | WO 00/77178 A1 | 12/2000 |
| WO | WO 01/03734 A1 | 1/2001 |
| WO | WO 01/10460 A1 | 2/2001 |
| WO | WO 01/10461 A1 | 2/2001 |
| WO | WO 01/10462 A1 | 2/2001 |
| WO | WO 01/13945 A1 | 3/2001 |
| WO | WO 01/29246 A1 | 4/2001 |
| WO | WO 01/34194 A1 | 5/2001 |
| WO | WO 01/39796 A1 | 6/2001 |
| WO | WO-01/62801 A2 | 8/2001 |
| WO | WO 01/77342 A1 | 10/2001 |
| WO | WO 01/97858 A2 | 12/2001 |
| WO | WO 02/02597 A2 | 1/2002 |
| WO | WO 02/04021 A1 | 1/2002 |
| WO | WO 02/031140 A1 | 4/2002 |
| WO | WO 02/34790 A1 | 5/2002 |
| WO | WO 02/046237 A2 | 6/2002 |
| WO | WO 02/060955 A2 | 8/2002 |
| WO | WO 02/064734 A2 | 8/2002 |
| WO | WO 02/088306 A2 | 11/2002 |
| WO | WO 02/088307 A2 | 11/2002 |
| WO | WO 02/096937 A2 | 12/2002 |
| WO | WO 02/096948 A2 | 12/2002 |
| WO | WO 03/002607 A1 | 1/2003 |
| WO | WO 03/009817 A2 | 2/2003 |
| WO | WO 03/011878 A2 | 2/2003 |
| WO | WO 03/016466 A2 | 2/2003 |
| WO | WO 03/061694 A1 | 7/2003 |
| WO | WO 03/068821 A2 | 8/2003 |
| WO | WO 03/070760 A2 | 8/2003 |
| WO | WO 03/084570 A1 | 10/2003 |
| WO | WO 03/085107 A2 | 10/2003 |
| WO | WO 03/085119 A1 | 10/2003 |
| WO | WO 2004/014953 A2 | 2/2004 |
| WO | WO-2004/020404 A2 | 3/2004 |
| WO | WO 2004/020454 A2 | 3/2004 |
| WO | WO 2004/032868 A2 | 4/2004 |

(56) References Cited

FOREIGN PATENT DOCUMENTS

| | | |
|---|---|---|
| WO | WO 2004/035607 A2 | 4/2004 |
| WO | WO 2004/056312 A2 | 7/2004 |
| WO | WO-2004/069870 A2 | 8/2004 |
| WO | WO 2005/053742 A1 | 8/2004 |
| WO | WO 2005/035586 A1 | 4/2005 |
| WO | WO 2005/035778 A1 | 6/2005 |
| WO | WO 2005/092925 A2 | 10/2005 |
| WO | WO 2005/100402 A1 | 10/2005 |
| WO | WO 2005/116220 A1 | 12/2005 |
| WO | WO 2006/029879 A2 | 3/2006 |
| WO | WO 2006/030220 A1 | 3/2006 |
| WO | WO 2006/044908 A2 | 4/2006 |
| WO | WO 2006/083689 A2 | 8/2006 |
| WO | WO 2006/131013 A2 | 12/2006 |
| WO | WO 2007/044323 A2 | 4/2007 |
| WO | WO-2007/059782 A1 | 5/2007 |
| WO | WO 2007/068429 A1 | 6/2007 |
| WO | WO 2007/110339 A1 | 10/2007 |
| WO | WO 2007/143711 A2 | 12/2007 |
| WO | WO 2008/005847 A2 | 1/2008 |
| WO | WO 2008/022349 A2 | 2/2008 |
| WO | WO 2008/025527 A1 | 3/2008 |
| WO | WO 2008/039944 A2 | 4/2008 |
| WO | WO 2008/063771 A2 | 5/2008 |
| WO | WO-2008/071394 A1 | 6/2008 |
| WO | WO 2008/077546 A1 | 7/2008 |
| WO | WO 2009/018411 A1 | 2/2009 |
| WO | WO 2009/040562 A1 | 4/2009 |
| WO | WO 2009/126616 A2 | 10/2009 |
| WO | WO 2010/033587 A2 | 3/2010 |
| WO | WO 2010/102251 A2 | 9/2010 |
| WO | WO 2010/115551 A1 | 10/2010 |
| WO | WO 2010/115553 A1 | 10/2010 |
| WO | WO 2011/066369 A2 | 6/2011 |
| WO | WO 2011/066371 A2 | 6/2011 |
| WO | WO 2011/116387 A1 | 9/2011 |
| WO | WO 2011/130377 A2 | 10/2011 |
| WO | WO 2012/075037 A1 | 6/2012 |
| WO | WO 2012/087835 A2 | 6/2012 |
| WO | WO 2012/088247 A2 | 6/2012 |
| WO | WO 2012/093125 A1 | 7/2012 |
| WO | WO 2012/096924 A1 | 7/2012 |
| WO | 2012/130831 A1 | 10/2012 |
| WO | 2012/143379 A1 | 10/2012 |
| WO | WO 2013/006244 A1 | 1/2013 |
| WO | WO 2013/012733 A1 | 1/2013 |
| WO | WO 2013/025853 A1 | 2/2013 |
| WO | WO 2013/026831 A1 | 2/2013 |
| WO | WO 2013/038156 A1 | 3/2013 |
| WO | WO 2013/039471 A1 | 3/2013 |
| WO | WO 2013/079174 A1 | 6/2013 |
| WO | WO 2013/113615 A1 | 8/2013 |
| WO | WO 2013/127816 A1 | 9/2013 |
| WO | WO 2013/177062 A2 | 11/2013 |
| WO | WO 2014/033074 A1 | 3/2014 |
| WO | WO 2014/039855 A1 | 3/2014 |
| WO | WO 2014/047231 A1 | 3/2014 |
| WO | WO 2014/052188 A1 | 4/2014 |
| WO | WO 2014/081955 A1 | 5/2014 |
| WO | WO 2014/082179 A1 | 6/2014 |
| WO | WO 2014/131694 A1 | 9/2014 |
| WO | WO 2014/131711 A1 | 9/2014 |
| WO | WO 2014/183973 A1 | 11/2014 |
| WO | WO 2014/189973 A2 | 11/2014 |
| WO | WO 2015/014884 A1 | 2/2015 |
| WO | WO 2015/063339 A1 | 5/2015 |
| WO | WO-2015/091144 A1 | 6/2015 |
| WO | WO 2015/095392 A1 | 6/2015 |
| WO | WO 2015/101588 A1 | 7/2015 |
| WO | WO 2016/020309 A1 | 2/2016 |
| WO | WO 2016/086189 A2 | 6/2016 |
| WO | WO 2016/160032 A1 | 10/2016 |
| WO | WO 2016/207240 A1 | 12/2016 |
| WO | WO-2017/055540 A1 | 4/2017 |
| WO | WO 2017/055542 A1 | 4/2017 |

OTHER PUBLICATIONS

Abysis, LM-PCR product'CL, Musmusculus, heavy chain, Accession No. 041242, 1998.

"ACTIT™ Non-radioactive cytotoxicity assay for flow cytometry (CellTechnology, Inc. Mountain View, CA)":6.

Acton R & D Systems Glial Cell Line-Derived Neurotrophic Factors: Advances in Research and Application 2011 Edition (1996).

Almagro and Fransson, "Humanization of antibodies" Front Biosci 13:1619-1633 (Jan. 1, 2008).

Anderson, K. et al., "Expression of Human B Cell-Associated Antigens on Leukemias and Lymphomas: A Model of Human B Cell Differentiation" Blood 63(6):1424-1433 (Jun. 1, 1984).

Anderson, W. et al., "Human Gene Therapy" Science 256(5058):808-813 (May 8, 1992).

Arai, R. et al., "Design of the linkers which effectively separate domains of a bifunctional fusion protein" Protein Eng 14(8):529-532 (Aug. 1, 2001).

Armour, K., et al., "Recombinant Human IgG Molecules Lacking Fc? Receptor I Binding and Monocyte Triggering Activities" Eur J Immunol 29(8):2613-2624 (Aug. 1, 1999).

Arnon, R. et al. Monoclonal Antibodies and Cancer Therapy "Chapter 3: Immunotherapy-Monoclonal Antibodies for Immunotargeting of Drugs in Cancer Therapy" (Proceedings of the Roche-UCLA Symposium; Park City, Utah-US, Jan. 26-Feb. 2, 1985), Reisfeld, R., and Sell, S., eds, New York, NY—US:Alan R. Liss, Inc.,:243-256 (1985).

Arzoo, K., et al., "Treatment of refractory antibody mediated autoimmune disorders with an anti-CD20 monoclonal antibody (rituximab)" Ann Rheum Dis 61(10):922-924 (Oct. 1, 2002).

Auner, H., et al., "Restoration of erythropoiesis by rituximab in an adult patient with primary acquired pure red cell aplasia refractory to conventional treatment" Br J Haematol 116(3):727-728 (Mar. 1, 2002).

Baca, M., et al., "Antibody humanization using monovalent phage display" J Biol Chem 272(16):10678-10684 (Apr. 18, 1997).

Bauduer, F., et al., "Rituximab: a very efficient therapy in cold agglutinins and refractory autoimmune haemolytic anaemia associated with CD20-positive, low-grade non-Hodgkin's lymphoma" Br J Haematol 112(4):1085-1086 (Mar. 1, 2001).

Berentsen, S., et al., "Favourable response to therapy with the anti-CD20 monoclonal antibody rituximab in primary chronic cold agglutinin disease" Br J Haematol 115(1):79-83 (Oct. 1, 2001).

Berentsen, S., et al., "Rituximab for primary chronic cold agglutinin disease: a prospective study of 37 courses of therapy in 27 patients" Blood 103(8):2925-2928 (Apr. 15, 2004).

Berlec, A., et al., "Current state and recent advances in biopharmaceutical production in *Escherichia coli*, yeasts and mammalian cells" J Ind Microbiol Biotechnol 40(3-4):257-274 (Apr. 1, 2013).

Bien-Ly, N., et al., "Transferrin receptor (TfR) trafficking determines brain uptake of TfR antibody affinity variants" J Exp Med 211(2):233-244 (Feb. 10, 2014).

Boado, R., et al., "Drug targeting of erythropoietin across the primate blood-brain barrier with an IgG molecular Trojan horse" J Pharm Exp Ther, Am Soc Pharm Exp Ther 333(3):961-969 (Jun. 1, 2010).

Boado, R., et al., "Engineering and expression of a chimeric transferrin receptor monoclonal antibody for blood-brain barrier delivery in the mouse" Biotechnol Bioeng 102(4):1251-1258 (Mar. 1, 2009).

Boado, R.J. et al., "Selective targeting of a TNFR decoy receptor pharmaceutical to the primate brain as a receptor-specific IgG fusion protein" J Biotechnol 146(1-2):84-91 (Mar. 1, 2010).

Boerner, P., et al., "Production of antigen-specific human monoclonal antibodies from in vitro-primed human splenocytes" J Immunol 147(1):86-95 (Jul. 1, 1991).

Bonifacino, J., et al., "Commonly Used Techniques: Molecular Biology Techniques" Curr Protocols in Cell Biol 8(1):1-4 (Oct. 1, 2000).

Brodeur, B., et al. Monoclonal Antibody Production Techniques and Applications "Chapter 4: Mouse-Human Myeloma Partners for the Production of Heterohybridomas" Schook, L., ed., New York, N.Y.—USA:Marcel Dekker, Inc.,:51-63 (Jan. 1, 1987).

(56) References Cited

OTHER PUBLICATIONS

Bruggemann, M., et al., "Comparison of the effector functions of human immunoglobulins using a matched set of chimeric antibodies" J Exp Med 166(5):1351-1361 (Nov. 1, 1987).
Brunhouse, R., et al., "Isotypes of IgG: comparison of the primary structures of three pairs of isotypes which differ in their ability to activate complement" Mol Immunol 16(11):907-917 (Nov. 1, 1979).
Bulbarelli, A., et al., "Trafficking of tail-anchored proteins: transport from the endoplasmic reticulum to the plasma membrane and sorting between surface domains in polarised epithelial cells" J Cell Science 115(Pt. 8):1689-1702 (Apr. 15, 2002).
Burton, D.R. et al., "The C1q receptor site on immunoglobulin G" Nature 288(5789):338-344 (Nov. 27, 1980).
Cambridge, G. et al., "B lymphocyte depletion in patients with rheumatoid arthritis: serial studies of immunological parameters" Arthritis Rheum (Abstract #1350), 46(9):5506 (Sep. 1, 2002).
Capel, P., et al., "Heterogeneity of human IgG Fc receptors" Immunomethods 4(1):25-34 (Feb. 1, 1994).
Carter, P. et al., "'Knobs-into-holes' provides a rational design strategy for engineering antibody CH3 domains for heavy chain heterodimerization" Immunotechnology 2(1):73 (Jan. 1, 1996).
Carter, P., et al., "Humanization of an anti-p185HER2 antibody for human cancer therapy" PNAS USA 89(10):4285-4289 (May 15, 1992).
Chari, R., et al., "Immunoconjugates containing novel maytansinoids: Promising anticancer drugs" Cancer Res 52(1):127-131 (Jan. 1, 1992).
Charlton, K.A., "Expression and isolation of recombinant antibody fragments in E. coli" Methods Mol Biol 248:245-254 (2003).
Chen, C., et al., "Enhancement and Destruction of Antibody Function by Somatic Mutation: Unequal Occurrence is Controlled by V Gene Combinatorial Associations" Embo J 14(12):2784-2794 (Jun. 15, 1995).
Chen, X., et al., "Fusion Protein Linkers: Property, Design and Functionality" Adv Drug Deliv Rev 65(10):1357-1369 (Oct. 15, 2013).
Chen, Y., et al., "Modern methods for delivery of drugs across the blood-brain barrier" Adv Drug Deliv Rev 64(7):640-665 (May 15, 2012).
Cheong et al., "Affinity enhancement of bispecific antibody against two different epitopes in the same antigen" Biochem Biophysic Res Comm 173(3):795-800 (Dec. 31, 1990).
The Chinese Office Action dated Dec. 29, 2018, in the related Chinese Appl. No. 201480069054.1. (The Machine-Generated Translations Included).
Chothia, C., et al., "Canonical structures for the hypervariable regions of immunoglobulins" J Mol Biol 196(4):901-917 (Aug. 20, 1987).
Chowdhury, P., "Engineering hot spots for affinity enhancement of antibodies" Methods Mol Biol 207:179-196 (2003).
Clackson, T. et al., "Making antibody fragments using phage display libraries" Nature 352(6336):624-628 (Aug. 15, 1991).
Clark, E., et al., "Role of Bp35 Cell Surface Polypeptide in Human B-cell Activation" PNAS USA 82(6):1766-1770 (Mar. 1, 1985).
Clynes, R., et al., "Fc receptors are required in passive and active immunity to melanoma" PNAS USA 95(2):652-656 (Jan. 20, 1998).
Coll, A., et al., "Rituximab therapy for the type B syndrome of severe insulin resistance" New Engl J Med 350(3):310-311 (Jan. 15, 2004).
Coloma, M.J., et al., "Position Effects of Variable Region Carbohydrate on the Affinity and In Vivo Behavior of an Anti-(1-6) Dextran Antibody" J Immunol 162(4):2162-2170 (Feb. 15, 1999).
Communication Pursuant to Article 94(3) EPC issued by the European Patent Office, dated Sep. 2, 2009, in related European Patent Appl. No. 06 829 502.1.
Comoglio, P. et al., "Drug development of MET inhibitors: targeting oncogene addiction and expedience" Nature 73:504-516 (Jun. 2008).
Cover page with English translation of Office Action issued by the Peruvian Patent Office, dated Feb. 10, 2010.

Cragg, M., et al., "Antibody Specificity Controls in Vivo Effector Mechanisms of Anti-CD20 Regents" Blood 103(7):2738-2743 (Apr. 1, 2004).
Cragg, M., et al., "Complement-mediated lysis by anti-CD20 mAb correlates with segregation into lipid rafts" Blood 101(3):1045-1052 (Feb. 1, 2003).
Cribbs et al., "Adjuvant-dependent modulation of Th1 and Th2 responses to immunization with b-amylo" Int Immunol 15(4):505-514 (2003).
Cross, A., et al., "Preliminary Results from a Phase II trial of Rituximab in MS" Abstract 8th Ann. Meeting of the Americas Committee, for Research and Treatment in Multiple Sclerosis, San Franciso, CA—US, pp. 20-21 (Oct. 19, 2003).
Cunningham, B., et al., "High-resolution epitope mapping of hGH-receptor interactions by alanine-scanning mutagenesis" Science 244(4908):1081-1085 (Jun. 2, 1989).
Dall'Acqua, W., et al., "Antibody humanization by framework shuffling" Methods 36(1):43-60 (May 1, 2005).
D'Arena, G., et al., "Late and long-lasting response in an adult chronic idiopathic thrombocytopenia purpura after extended course of rituximab" Leuk Lymphoma 44(3):561-562 (Mar. 1, 2003).
De Haas, M., et al., "Fc? receptors of phagocytes" J Lab Clin Med 126(4):330-341 (Oct. 1, 1995).
De Vita, S., et al., "Efficacy and Safety of Rituximab Treatment in Type II Mixed Cryoglobulinemia" Abstract (Arthritis & Rheum., Abstract #469,) ACR Concurrent Session Vaculitis: Novel Treatment and Pathogenesis, New Orleans, LA—US, pp. S206 (Oct. 26, 2002).
De Vita, S., et al., "Efficacy of Selective B Cell Blockade in the Treatment of Rheumatoid Arthritis" Arthritis Rheum 46(8):2029-2033 (Aug. 1, 2002).
Deyev, S., et al., "Modern Technologies for Creating Synthetic Antibodies for Clinical Application" Acta Naturae 11(1):32-50 (Apr. 1, 2009).
Di Zenzo, G. et al., "The Intracellular and Extracellular Domains of BP180 Antigen Comprise Novel Epitopes Targeted by Pemphigoid Gestationis Autoantibodies" J. of Investigative Dermatology 127:864-873 (Mar. 19, 2006).
Dubowchik, G., et al., "Doxorubicin immunoconjugates containing bivalent, lysosomally-cleavable dipeptide linkages" Bioorg Med Chem Lett 12(11):1529-1532 (Jun. 3, 2002).
Duncan, A., et al., "The Binding Site for C1q on IgG" Nature 332(6166):738-740 (Apr. 21, 1988).
Dupuy, A., et al., "Treatment of refractory pemphigus vulgaris with rituximab (anti-CD20 monoclonal antibody)" Arch Dermatol 140(1):91-96 (Jan. 1, 2004).
Edwards, B., et al., "The remarkable flexibility of the human antibody repertoire; isolation of over one thousand different antibodies to a single protein, BLyS" J Mol Biol 334(1):103-118 (Nov. 14, 2003).
Edwards, J., et al., "B-lymphocyte depletion therapy in rheumatoid arthritis and other autoimmune disorders" Biochem Soc Trans 30(4):824-828 (Aug. 1, 2002).
Edwards, J., et al., "Efficacy and safety of Rituximab, a B-cell targeted chimeric monoclonal antibody: A randomized, placebo-controlled trial in patients with rheumatoid arthritis" Arthritis Rheum (Abstract #446), 46(9):5197 (2002).
Edwards, J., et al., "Sustained Improvement in Rheumatoid Arthritis Following a Protocol Designed to Deplete B Lymphocytes" Rheumatology 40(2):205-211 (Feb. 1, 2001).
Einfeld, D.A. et al., "Molecular Cloning of the Human B Cell CD20 Receptor Predicts a Hydrophobic Protein with Multiple Transmembrane Domains" Embo J 7(3):711-717 (Mar. 1, 1988).
Eisenberg, R. et al., "SLE—Rituximab in lupus" Arthritis Res Ther 5(4):157-159 (2003).
Emery et al., "Sustained Efficacy at 48 Weeks after Single treatment Course of Rituximab in patients with Rheumatoid Arthritis" Arthritis Rheum ((Abstract #1095)), 48(9 Suppl S439) (2003).
Endo et al., "Glycosylation of the variable region of immunoglobulin G—site specific maturation of the sugar chains" Mol Immunol 32(13):931-940 (1995).

(56) References Cited

OTHER PUBLICATIONS

English translation Notice of the Result of Substantive Examination of a Patent Application issued by the Patents Office of the Cooperation Council for the Arab States of the Gulf GCC, dated Jan. 2, 2010, in related Appl. No. 7376.
English translation of Japanese Office Action (Notification of Reasons for Rejection), issued May 28, 2019, in the related Japanese Patent Application No. 2018-516702.
The English translation of the Japanese Office Action, dated Feb. 7, 2019, in the related Japanese Appl. No. 2016-541174.
The English translation of the Japanese Office Action, dated Nov. 20, 2018, in the related Japanese Appl. No. 2016-544800.
English translation of Notice of Grounds for Rejection in Japanese Patent Application No. 2009-053951, dispatched on Aug. 11, 2011.
English translation of Notice of Preliminary Rejection and cited references issued by the Korean Patent Office, dated Jan. 13, 2011, in related Korean Patent Application No. 7012289/2008.
English translation of Office Action and Search Report issued by the Taiwanese Patent Office, dated Jul. 22, 2009, in related Patent Application No. 095146304.
English translation of Office Action issued by Israeli Patent Office dated Jul. 14, 2010, in related Israeli Patent Application No. 191004.
English translation of Office Action issued by the Mexican Patent Office, dated Mar. 18, 2011, in related Mexican Patent Appl. No. MX/a/2008/006948.
English translation of Office Action issued by the Pakistani Patent Office, dated Jul. 30, 2009, in related Pakistani Patent Appl. No. 162912006.
English translation of Office Action issued by the Russian Patent Office, dated Mar. 23, 2011, in related Russian patent Application 2008 128 138.
English translation of Office Action issued by the Russian Patent Office, dated Sep. 23, 2010, in related Russian Patent Application 2008 128 138.
English translation of Office Action issued by the State Intellectual Property Office of The PRC, dated Dec. 28, 2010, in related Chinese Application No. 200680046307.9.
English translation of Office Action issued by the Taiwan Patent Office in ROC (Taiwan) Patent Application No. 095146304, dated Aug. 20, 2012.
English translation of Office Action—Preliminary Examination Report issued by the Ukrainian Patent Office, dated Jun. 14, 2011, in related Ukrainian Patent Application No. a 20080879.
Eriksson, "Short-term outcome and safety in 5 patients with ANCA-positive vasculitis treated with rituximab" Kidney Blood Press R (Abstract p. 87), 26:294 (2003).
Examiner's First Report issued by the Australian Patent Office, dated Aug. 23, 2010, in related Australian patent application No. 2006326301.
Felgenhauer et al., "Protein size and cerebrospinal fluid composition" Klin. Wschr 52:1158-1164 (1974).
Flatman, S., et al., "Process analytics for purification of monoclonal antibodies" J Chromatogr 848(1):79-87 (Mar. 15, 2007).
Frenkel et al., "High affinity binding of monoclonal antibodies to the sequential epitope EFRH of b-amyloid peptide is essential for modulation of fibrillar aggregation" Journal of Immunology 95:136-142 (1999).
Frenkel et al., "Immunization against Alzheimer's b-amyloid plaques via EFRH phage administration" PNAS 97(21):11455-11459 (2000).
Frenkel et al., "N-terminal EFRH sequence of Alzheimer's b-amyloid peptide represents the epitope of its anti-aggregating antibodies" Journal of Neuroimmunology 88:85-90 (1998).
Gazzano-Santoro et al., "A non-radioactive complement-dependent cytotoxicity assay for anti-CD20 monoclonal antibody" Journal of Immunological Methods 202(2):163-171 (Mar. 28, 1997).
Gerngross, T,U., "Advances in the production of Human Therapeutic Proteins in yeasts and filamentous fungi," Nat. biotech. 22 (2004) 1409-1414.
Gessner, J., et al., "The IgG Fc Receptor Family" Ann Hematol 76(6):231-248 (Jun. 1, 1998).

Ghoshal et al., "Tau-66: evidence for a novel tau conformation in Alzheimer's disease" Journal of Neurochemistry 77:1372-1385 (2001).
Glenner et al., "Alzheimer's Disease and Dowi\'s Syndrome: Sharing of a Unique Cerebrovascular Amyloid Fibril Protein" Biochem Biophys Res Commun. 122(3):1131-1135 (1984).
Gorman, C. et al., "Does B cell depletion have a role to play in the treatment of systemic lupus erythematosus?" Lupus 13(5):312-316 (2004).
Graham, F., et al., "Characteristics of a Human Cell Line Transformed by DNA from Human Adenovirus Type 5" J Gen Virol 36(1):59-74 (Jul. 1, 1977).
Gulko, L.B., et al., "The Obtaining of the VNTR22 (MUC1) Polypeptide Preparation with the Potential Antitumor Vaccination Activity" Biotechnology 3:3-8 ( 2000).
Guyer, R., et al., "Immunoglobulin binding by mouse intestinal epithelial cell receptors" J Immunol 117(2):587-593 (Aug. 1, 1976).
Hardy, J., "Amyloid, the presenilins and Alzheimer's disease" Trends Neurosci 20(4):154-159 (Apr. 1, 1997).
Harper et al., "Models of Amyloid Seeding in Alzheimer's Disease and Scrapie: Mechanistic Truths and Physiological Consequences of the Time-Dependent Solubility of Amyloid Proteins" Annu. Rev. Biochem. 66:385-407 (1997).
Hawker, K et al., "Rituximab in patients with primary progressive multiple sclerosis: results of a randomized double-blind placebo-controlled multicenter trial" Ann Neurol 66(4):460-471 (Oct. 1, 2009).
Hellstrom et al., "Strong antitumor activities of IgG3 antibodies to a human melanoma-associated ganglioside" Proceedings of the National Academy of Sciences 82(5):1499-1502 (Mar. 1, 1985).
Hellstrom, I., et al., "Antitumor effects of L6, an IgG2a antibody that reacts with most human carcinomas" PNAS USA 83(18):7059-7063 (Sep. 1, 1986).
Hellstrom, K., et al. Controlled Drug Delivery: Fundamentals and Applications "Chapter 15: Antibodies for Drug Delivery" Robinson, J., and Lee, V., eds., Second edition, Basel, CH and New York, NY—US:Marcel Dekker, Inc., vol. 29:623-642 (1987).
Hezareh, M., et al., "Effector function activities of a panel of mutants of a broadly neutralizing antibody against human immunodeficiency virus type 1." J Virol 75(24):12161-12168 (Dec. 1, 2001).
Higashida, J., et al., "Treatment of DMARD-Refractory Rheumatoid Arthritis With Rituximab" Poster (Abstract #LB11) Annual Scientific Meeting of the American College of Rheumatology, New Orleans, LA—US, ( Oct. 24-29, 2002).
Hinman, L., et al., "Preparation and characterization of monoclonal antibody conjugates of the calicheamicins: A novel and potent family of antitumor antibiotics" Cancer Res 53(14):3336-3342 (Jul. 15, 1993).
Hoogenboom, H., et al., "Overview of antibody phage-display technology and its applications" Methods Mol Biol 178:1-37 (Jan. 1, 2002).
Hust, M., et al., "Single chain Fab (scFab) fragment" BMC Biotechnol 7(14):1-15 (Mar. 8, 2007).
Idusogie, E.E., et al., "Mapping of the C1q Binding Site on Rituxan, a Chimeric Antibody with a Human IgG1 Fc" J Immunol 164(8):4178-4184 (Apr. 15, 2000).
International Search Report and Written Opinion (Mar. 6, 2014) for International Patent Application No. PCT/EP2013/067595.
International Preliminary Report on Patentability issued on Apr. 3, 2018, for PCT Application No. PCT/EP2016/073411, filed on Sep. 30, 2016, 7 pages.
International Search Report and Written Opinion for PCT/EP 2016/073413 mailed on Jan. 9, 2017.
International Search Report and Written Opinion prepared by the European Patent Office dated Apr. 8, 2015, for International Application No. PCT/EP2014/079353.
International Search Report and Written Opinion prepared by the European Patent Office dated Dec. 23, 2016, for International Application No. PCT/EP2016/064460.
International Search Report for PCT/EP 2016/073413 mailed on Jan. 9, 2017.

(56) References Cited

OTHER PUBLICATIONS

International Search Report PCT/EP2016/073411 dated Dec. 14, 2016.
Janeway, C., "Autoimmune disease: immunotherapy by peptides?" Nature 341(6242):482-483 (Oct. 12, 1989).
Jarrett, J.T., et al., "Seeding 'One-Dimensional Crystallization' of Amyloid: A Pathogenic Mechanism in Alzheimer's Disease and Scrapie?" Cell 73(6):1055-1058 (Jun. 18, 1993).
Jayne, D., "Current attitudes to the therapy of vasculitis" Kidney Blood Press R 26(4):231-239 (2003).
Jayne, D., et al., "B-cell depletion with rituximab for refractory vasculitis" Kidney Blood Press R (Abstract p. 88), 26:294-295 (2003).
Jeffrey, S., et al., "Dipeptide-based highly potent doxorubicin antibody conjugates" Bioorg Med Chem Lett 16(2):358-362 (Jan. 15, 2006).
Jost, C.R., et al., "Mammalian expression and secretion of functional single-chain Fv molecules" J Biol Chem 269(42):26267-26273 (Oct. 21, 1994).
Kabat, E. et al., "Sequences of Proteins of Immunological Interest" 1 (Fifth Edition):647-660 (1991).
Kabat, E. et al., "Sequences of Proteins of Immunological Interest" 1 (Fifth Edition):661-723 (1991).
Kabat, E.A, et al. Sequences of Proteins of Immunological Interest 5th edition, NIH,:Pubication 91-3242, 2 pages (1991).
Kam, N. et al., "Carbon nanotubes as multifunctional biological transporters and near-infrared agents for selective cancer cell destruction" PNAS USA 102(33):11600-11605 (Aug. 16, 2005).
Kanda, Y., et al., "Comparison of cell lines for stable production of fucose-negative antibodies with enhanced ADCC" Biotechnol Bioeng 94(4):680-688 (Jul. 5, 2006).
Kashmiri et al., "SDR grafting—a new approach to antibody humanization" Methods 36:25-34 (May 1, 2005).
Kay, B.K., et al., "An M13 phage library displaying random 38-amino-acid peptides as a source of novel sequences with affinity to selected targets" Gene 128(1):59-65 (Jun. 15, 1993).
Kazkai, H., et al., "Anti B cell Therapy (rituximab) in the treatment of autoimmune diseases" Curr Opin Pharmacol 4(4):398-402 (Aug. 1, 2004).
Keogh, K. et al., "Rituximab for Remission Induction in Severe ANCA-Associated Vasculities. A Report of a Prospective Open-Label Pilot Trial in 10 Patients" Abstract (Abstract 605) American College of Rheumatology, Session title: Vasculitis, Orlando, Florida—US, pp. 1 ( Oct. 18, 2004).
Kim, J., et al., "Localization of the site of the murine IgG1 molecule that is involved in binding to the murine intestinal Fc receptor" Eur J Immunol 24(10):2429-2434 (Oct. 1, 1994).
Kindt, T., et al. Kuby Immunology "Part II: Generation of B-Cell and T-Cell Response, Chapter 4: Antigen and Antibodies" Kindt, T., Goldsby, R., eds, Sixth edition, New York, N.Y.—USA:W. H. Freeman and Company,:91 (2007).
King, H.D., et al., "Monoclonal antibody conjugates of doxorubicin prepared with branched peptide linkers: Inhibition of aggregation by methoxytriethyleneglycol chains" J Med Chem 45(19):4336-4343 (Sep. 12, 2002).
Kjeldsen, T., et al., "A removable spacer peptide in an alpha-factor-leader/insulin precursor fusion protein improves processing and concomitant yield of the insulin precursor in *Saccharomyces cerevisiae*" Gene 170(1):107-112 (Apr. 17, 1996).
Klein C. et al., "Progress in overcoming the chain association issue in bispecific heterodimeric IgG antibodies" MABS 4(6):653-663 (Nov. 1, 2012).
Klemmer, N., et al., "Treatment of antibody mediated autoimmune disorders with a Anti-CD20 monoclonal antibody Rituximab" Arthritis Rheum (Abstract #1623), 48( Suppl 9):S624 (Sep. 1, 2003).
Klimka, A., et al., "Human anti-CD30 recombinant antibodies by guided phage antibody selection using cell panning" Br J Cancer 83(2):252-260 (Mar. 1, 2000).

Knappik, A., et al., "Fully Synthetic Human Combinatorial Antibody Libraries (HuCAL) Based on Modular Consensus Frameworks and CDRs Randomized with Trinucleotides" J Mol Biol 296(1):57-86 (Feb. 11, 2000).
Kneitz, C., et al., "Effective B cell depletion with rituximab in the treatment of autoimmune diseases" Immunobiology 206(5):519-527 (Dec. 1, 2002).
Kontermann, R., "Dual targeting strategies with bispecific antibodies" MABS 4(2):182-197 (Mar. 1, 2012).
Koo, E.H., et al., "Amyloid diseases: Abnormal protein aggregation in neurodegeneration" PNAS USA 96(18):9989-9990 (Aug. 31, 1999).
Kozbor, D., et al., "A Human Hybrid Myeloma for Production of Human Monoclonal Antibodies" J Immunol 133(6):3001-3005 (Dec. 1, 1984).
Kratz, F., et al., "Prodrugs of anthracyclines in cancer chemotherapy" Curr Med Chem 13(5):477-523 (Mar. 1, 2006).
Kuby J. ed. Immunology, Third Edn. 1997, WH Freeman & Co., New York, pp. 131-135.
Kussie et al., "A Single Engineered Amino Acid Substitution Changes Antibody Fine Specificity" Journal of Immunology 152:146-152 (1994).
Lake and Dionne et al. Burger's Medicinal Chemistry and Drug Discovery "6" Abraham, 6th edition, Hoboken:John Wiley & Sons, Inc., vol. 5:223-247 (2003).
Layios, N., et al., "Remission of severe cold agglutinin disease after Rituximab therapy" Leukemia 15(1):187-188 (Jan. 1, 2001).
Leandro, M. et al., "An open study of B lymphocyte depletion in systemic lupus erythematosus" Arthritis Rheum 46(10):2673-2677 (Oct. 1, 2002).
Leandro, M., et al., "B cell repopulation occurs mainly from naive B cells in patients with rheumatoid arthritis and systemic lupus erythematosus treated with rituximab" Arthritis Rheum (Abstract #1160), 48( Suppl 9):S464 (Oct. 27, 2003).
Leandro, M., et al., "Clinical outcome in 22 patients with rheumatoid arthritis treated with B lymphocyte depletion" Ann Rheum Dis 61(10):883-888 (Oct. 1, 2002).
Leandro, M., et al., "Treatment of refractory lupus nephritis with B lymphocyte depletion" Arthritis Rheum (Abstract #924), 48( Suppl Supplement 9):S378 (2003).
Leibiger, H., et al., "Variable domain-linked oligosaccharides of a human monoclonal IgG : structure and influence on antigen binding" Biochem J 338(Pt.2):529-538 (Mar. 1, 1999).
Levine, "A Pilot Study of Rituximab Therapy for Refractory Dermatomyositis" Arthritis Rheum (Abstract No. 1299), 46( Suppl 9):S488-S489 (2002).
Levine, T., et al., "IgM antibody-related polyneuropathies: B-cell depletion chemotherapy using Rituximab" Neurology 52(8):1701-1704 (May 12, 1999).
Li et al., "Antibody conjugation via one and two C-terminal selenocysteines" Methods 65:133-138 (2014).
Li, H. et al., "Optimization of humanized IgGs in glycoengineered Pichia pastoris" Nature biotechnology (Epub Jan. 22, 2006), 24(2):210-215 (Feb. 1, 2006).
Li, G. et al., "Amplification and sequence analysis of the brain derived neurotropic factor (BDNF) gene from the Baiji (*Lipotes vexillifer*)" Acta Theriologica Sinica (Chinese with English Abstract), 26(1):38-43 (Jan. 1, 2006).
Li, J., et al., "Human antibodies for immunotherapy development generated via a human B cell hybridoma technology" PNAS USA 103(10):3557-3562 (Mar. 7, 2006).
Liang and Tedder et al. Wiley Encyclopedia of Molecular Medicine John Wiley & Sons, Inc., New York:John Wiley,:562-564 (Jan. 15, 2002).
Lim, Y. et al., "Engineering mammalian cells in bioprocessing—current achievements and future perspectives" Biotechnol. Appl. Biochem. 55:175-189 ( 2010).
Lim et al., "anti-Toxoplasma gondii tachyzoite single-chain variable fragment antibody, partial [synthetic construct]," GenBank_NCBI_ Accession No. AEX30828.1.

(56) References Cited

OTHER PUBLICATIONS

Lloyd, C., et al., "Modelling the human immune response: performance of a 1011 human antibody repertoire against a broad panel of therapeutically relevant antigens" Protein Eng Des Sel 22(3):159-168 (Mar. 1, 2009).

Lo, K.M., et al., "High level expression and secretion of Fc-X fusion proteins in mammalian cells" Protein Eng 11(6):495-500 (Jun. 1, 1998).

Lode, H.N., et al., "Targeted therapy with a novel enediyene antibiotic calicheamicin V11 effectively suppresses growth and dissemination of liver metastases in a syngeneic model of murine neuroblastoma" Cancer Res 58(14):2925-2928 (Jul. 15, 1998).

Lonberg, "Fully human antibodies from transgenic mouse and phage display platforms" Current opinion in immunology (Epub Jul. 21, 2008), 20(4):450-459 (Aug. 2008).

Lonberg, N., "Human antibodies from transgenic animals" Nat Biotechnol 23(9):1117-11125 (2005).

Looney, R. J., "Treating human autoimmune disease by depleting B cells" Ann Rheum Dis 61(10):863-866 (Oct. 1, 2002).

Lu, D., et al., "Acquired antagonistic activity of a bispecific diabody directed against two different epitopes on vascular endothelial growth factor receptor 2" J Immunol Methods 230(1-2):159-171 (Nov. 19, 1999).

Lukas, T. J., et al., "Inhibition of C1-mediated immune hemolysis by monomeric and dimeric peptides from the second constant domain of human immunoglobulin G" J Immunol 127(6):2555-2560 (Dec. 1, 1981).

Lund, J., et al., "Oligosaccharide-protein interactions in IgG can modulate recognition by Fc gamma receptors" Faseb J. 9(1):115-119 (Jan. 1, 1995).

MacCallum, R., et al., "Antibody-antigen Interactions: Contact Analysis and Binding Site Topography" J Mol Biol 262(5):732-745 (Oct. 11, 1996).

Martin, F., et al., "Pathogenic Roles of B Cells in Human Autoimmunity: Insights from the Clinic" Immunity 20(5):517-527 (May 1, 2004).

Mather, J. et al., "Culture of Testicular Cells in Hormone-Supplemented Serum-Free Medium" Ann NY Acad Sci 383:44-68 (1982).

Mather, J., "Establishment and Characterization of Two Distinct Mouse Testicular Epithelial Cell Lines" Biol Reprod 23:243-252 (1980).

Meder, D., et al., "Gp135/podocalyxin and NHERF-2 participate in the formation of a preapical domain during polarization of MDCK cells" J Cell Biol 168(2):303-313 (Jan. 17, 2005).

Merchant et al., "An efficient route to human bispecific IgG" Nat Biotechnol 16(7):677-681 (Jul. 1, 1998).

Morgan, A, et al., "The N-terminal end of the CH2 domain of chimeric human IgG1 anti-HLA-DR is necessary for C1q, Fc gamma RI and Fc gamma RIII binding" Immunology 86(2):319-324 (Oct. 1, 1995).

Morrison, S., et al., "Chimeric human antibody molecules: Mouse antigen-binding domains with human constant region domains" PNAS USA 81(21):6851-6855 (Nov. 1, 1984).

Nagy, A., et al., "Stability of cytotoxic luteinizing hormone-releasing hormone conjugate (AN-152) containing doxorubicin 14-O-hemiglutarate in mouse and human serum in vitro: implications for the design of preclinical studies" PNAS USA 97(2):829-834 (Jan. 18, 2000).

NCBI et al., "Sequence Viewer v3.1 Report—Complete Nucleotide Sequence of the High Molecular Weight Human IGF-I mRNA" (NCBI_IGF-1_P01343),:1-3 (Nov. 4, 2016).

Nestler, E.J., et al. Molecular Neuropharmacology: A Foundation for Clinical Neuroscience "Chapter 8: Atypical Neurotransmitters" Fourth edition, New York, N.Y.—USA:McGraw-Hill Publishers,:211-219 (2009).

Ni, J. et al., "Research progress and future perspectives in antibodomics and antibodomic drugs" Xiandai Mianyixue 26(4):265-268 (2006).

Niewoehner, J., et al., "Increased Brain Penetration and Potency of a Therapeutic Antibody Using a Monovalent Molecular Shuttle" Neuron 81(1):49-60 (Jan. 8, 2014).

Office Action issued by Canadian Patent Office, dated Oct. 31, 2011, in related Canadian Patent Appl. No. 2632828.

Office Action issued by the Chilean Patent Office, dated Dec. 11, 2006, in related Chilean Appl. No. 3436-2006.

Office Action issued by the Colombian Patent Office in Application No. 2008 049920-A, dated Sep. 6, 2012.

Office Action issued by the Malaysian Patent Office in Application No. PI 20081349, dated Nov. 14, 2012.

Office Action issued by the New Zealand Patent Office, dated Apr. 13, 2010, in related New Zealand Patent Appl. No. 568241.

Offner, H. et al., "T cell receptor peptide therapy triggers autoregulation of experimental encephalomyelitis" Science 251(4992):430-432 (Jan. 25, 1991).

Ohno et al., "Antigen-binding specificities of antibodies are primarily determined by seven residues of VH," Proc Natl Acad Sci U S A, May 1985,; 82(9):2945-9.

Okazaki, A., et al., "Fucose depletion from human IgG1 oligosaccharide enhances binding enthalpy and association rate between IgG1 and FcgammaRIIIa" J Mol Biol 336(5):1239-1249 (Mar. 5, 2004).

O'Nuallain, B. et al., "Conformational Abs recognizing a generic amyloid fibril epitope" PNAS 99(3):1485-1490 (2002).

Osbourn et al., "From rodent reagents to human therapeutics using antibody guided selection" Methods 36(1):61-68 (May 1, 2005).

Osol, A. Remington's Pharmaceutical Sciences 16 edition, (1980).

Pace, C., et al., "How to measure and predict the molar absorption coefficient of a protein" Protein Sci 4(11):2411-2423 (Nov. 1, 1995).

Padlan et al., "A possible procedure for reducing the immunogenicity of antibody variable domains while preserving their ligand-binding properties" Molecular immunology (Apr.-May 1991), 28(4-5):489-498.

Palcula, A. et al "Genetic Analysis of Protein Stability and Function" Annu. Rev. Genet. :23:189-310 (1989).

Pardridge, W.M. et al., "Blood—brain barrier drug delivery of IgG fusion proteins with a transferrin receptor monoclonal antibody" Expert Opin Drug Del 12(2):207-222 (Feb. 1, 2015).

Pardridge, W.M. et al., "Drug transport across the blood-brain barrier" J Cerebral Blood Flow Metab 32:1959-1972 (2012), 14 pages.

Pardridge, W.M., et al., "Selective Transport of an Anti-Transferrin Receptor Antibody Through the Blood-Brain Barrier in Vivo" J Pharmacol Exp Ther 259(1):66-70 (Oct. 1, 1991).

Pardridge, W.M., "Re-Engineering Biopharmaceuticals for Delivery to Brain with Molecular Trojan Horses" Bioconjugate Chem 19(7):1327-1338 (Jun. 12, 2008).

Paul, W., Fundamental Immunology "Chapter 9: Structure and Function of Immunoglobins" Paul, W., ed., Third edition, New York, N. Y.—USA:Raven Press,:242, 292-295 (Jan. 1, 1993).

Patent examination report 1, mailed on May 23, 2024, in related New Zealand Appl. No. 779858.

Penichet and Morrison et al. Wiley Encyclopedia of Molecular Medicine (Section: Chimeric, Humanized and Human Antibodies), John Wiley & Sons Inc., New York:John Wiley,:214-216 (2002).

Perlman, S., et al., "Glycosylation of an N-Terminal Extension Prolongs the Half-Life and Increases the in Vivo Activity of Follicle Stimulating Hormone" J Clin Endocrino Metabol 88(7):3227-3235 (Jul. 1, 2003).

Perotta, A., et al., "Response of Chronic Relapsing ITP of 10 years duration to Rituximab" Blood (Abstract #3360 ; Part 1-2), 92(10 Suppl 1):88b (Nov. 15, 1998).

Perotta, A., et al., Rituxan in the Treatment of Chronic Idiopathic Thrombocytopenia Blood (Abstract #49), 94(14):4a (1999).

Pestronk, A., et al., "Treatment of IgM antibody associated polyneuropathies using rituximab" J Neurol Neurosurg Psychiatry 74(4):485-489 (Apr. 1, 2003).

Petkova, S., et al., "Enhanced half-life of genetically engineered human IgG1 antibodies in a humanized FcRn mouse model: potential application in humorally mediated autoimmune disease" Int Immunol 18(12):1759-1769 (Dec. 1, 2006).

(56) References Cited

OTHER PUBLICATIONS

Portolano, S., et al., "Lack of promiscuity in autoantigen-specific H and L chain combinations as revealed by human H and L chain 'roulette'" J Immunol 150(3):880-887 (Feb. 1, 1993).
Pranzatelli, M., et al., "CSF B-Cell Over-Expansion in Paraneoplastic Opsoclonus-Myoclonus: Effect of Rituximab, an Anti-B-Cell Monoclonal Antibody" Neurology (Abstract No. P05.128), 60(5 Suppl 1):A395 (Mar. 1, 2003).
Press, O., et al., "Monoclonal Antibody 1F5 (Anti-CD20) Serotherapy of Human B Cell Lymphomas" Blood 69(2):584-591 (Feb. 1, 1987).
Presta, L., et al., "Humanization of an Antibody Directed Against IgE" J Immunol 151(5):2623-2632 (Sep. 1, 1993).
Price et al., "Genetic Neurodegenerative Diseases: The Human Illness and Transgenic Models" Science 282(5391):1079-1083 (1988).
Promega, Inc. et al., "Cyto Tox 96® non-radioactive cytotoxicity assay—Technical Bulletin" (G1780—Instructions for Use of Product, Revised),:1-21 (Jul. 1, 2016).
Queen, C., et al., "A humanized antibody that binds to the interleukin 2 receptor" Proceedings of the National Academy of Sciences 86(24):10029-10033 (Dec. 1989).
R.&D Systems, "Gilial Cell Line-derived Neuropathic Factor (GDNF)", originally published in R&D Systems' 1996 Catalog.
R&D Systems, "Glial Cell Line-derived Neurotrophic Factor (GDNF)," https://www.rndsystems.com/resources/articles/glial-cell-line-derived-neurotrophic-factor -gdnf, May 14, 2019.
Raju, T., "Glycosylation variations with expression systems and their impact on biological activity of therapeutic immunoglobulins" Bioprocess Intl 1:44-53 (Apr. 1, 2003).
Ratanatharathorn, V., et al., "Anti-CD20 chimeric monoclonal antibody treatment of refractory immune-mediated thrombocytopenia in a patient with chronic graft-versus-host disease" Ann Intern Med 133(4):275-279 (Aug. 15, 2000).
Ravetch and Kinet et al., "Fc receptors" Ann. Rev. Immunol. 9:457-492 (1991).
Ravetch, J. et al., "IgG Fc receptors" Ann Rev Immunol 19:275-290 (Apr. 1, 2001).
Reff, M.E. et al., "Depletion of B cells in vivo by a chimeric mouse human monoclonal antibody to CD20" Blood 83(2):435-445 (Jan. 15, 1994).
Remington, J., et al. Remington's Pharmaceutical Sciences (Table of Contents, total in 4 pages), OSOL , eds., 16th edition, Easton, PA:Mack Publishing Company, (Jan. 1, 1980).
Richards et al., "PS2APP Transgenic Mice, Coexpressing hPS2mut and hAPPswe, Show Age-Related Cognitive Deficits Associated with Discrete Brain Amyloid Deposition and Inflammation" Journal of Neuroscience 23(26):8989-9003 (2003).
Ridgway, J., et al., "Knobs-into-holes' engineering of antibody CH3 domains for heavy chain heterodimerization" Protein Engineering 9(7):617-621 (Jul. 1996).
Riechmann, L., "Reshaping human antibodies for therapy" Nature 332(6162):323-327 (Mar. 24, 1988).
Ripka, J., et al., "Two chinese hamster ovary glycosylation mutants affected in the conversion of GDP-mannose to GDP-fucose" Arch Biochem Biophys 249(2):533-545 (Sep. 1, 1986).
Rosok, M., et al., "A combinatorial library strategy for the rapid humanization of anticarcinoma BR96 Fab" J Biol Chem 271(37):22611-22618 (Sep. 13, 1996).
Routier, F., et al., "The glycosylation pattern of a humanized IgGI antibody (D1.3) expressed in CHO cells" Glycoconjugate J 14(2):201-207 (Feb. 1, 1997).
Rudikoff, S., et al., "Single amino acid substitution altering antigen-binding specificity" PNAS USA 79(6):1979-1983 (Mar. 1, 1982).
Saleh, M., et al., "A pilot study of the anti-CD20 monoclonal antibody rituximab in patients with refractory immune thrombocytopenia" Semin Oncol 27(6 Suppl 12):99-103 (Dec. 1, 2000).
Sambrook, J., et al. Molecular Cloning: A Laboratory Manual Second edition, New York:Cold Spring Harbor Laboratory Press, (Jan. 1, 1989).

Schaefer, W., et al., "Immunoglobulin domain crossover as a generic approach for the production of bispecific IgG antibodies" PNAS USA 108(27):11187-11192 (Jul. 5, 2011).
Schier, R. et al., "Isolation of picomolar affinity anti-c-erbB-2 single-chain Fv by molecular evolution of the complementarity determining regions in the center of the antibody binding site" J Mol Biol 263(4):551-567 (Nov. 8, 1996).
Schneider, C., et al., "Primary structure of human transferrin receptor deduced from the mRNA sequence" Nature 311(5987):675-678 (Oct. 18, 1984).
Seidah, N.G., et al., "Cellular processing of the nerve growth factor precursor by the mammalian pro-protein convertases" Biochem J 314(Pt. 3):951-960 (Mar. 15, 1996).
Selkoe, D.J., "Cell biology of the amyloid beta-protein precursor and the mechanism of Alzheimer's disease" Ann Rev Cell Biol 10:373-403 (Nov. 1, 1994).
Shamenkov D A et al., "Prospects of using apolipoprotein-mediated transport of drugs across the blood-brain barrier or improving pharmacotherapy," Pharmateca, No. 20, pp. 95-98, 2010. {The English abstract included).
Sheeley, D., et al., "Characterization of Monoclonal Antibody Glycosylation: Comparison of Expression Systems and Identification of Terminal ?-Linked Galactose" Anal Biochem 247(1):102-110 (Apr. 5, 1997).
Shen-Xin et al., "Study on in vitro anti-tumor effect of anti-human transferrin receptor monoclonal antibody" Chin. J. Cell Mol Immunol (English Abstract), 24(2):144-146 (2008) (The English abstract included.).
Shields et al., "High Resolution Mapping of the Binding Site on Human IgG1 for Fc?RI, Fc?RII, Fc?RIII, and FcRn and Design of IgG1 Variants with Improved Binding to the Fc?R" J Biol Chem 276(9):6591-6604 (2001).
Silverman and Weisman et al., "Rituximab therapy and autoimmune disorders: prospects for anti-B cell therapy" Arthritis Rheum 48(6):1484-1492 (Jun. 2003).
Sims, M., et al., "A Humanized CD18 Antibody Can Block Function Without Cell Destruction" J Immunol 151(4):2296-2308 (Aug. 15, 1993).
Singapore Examination Report issued by the Danish Patent Office, dated Jan. 3, 2011, in Appl. No. 200803302-9.
Singapore Written Opinion and Search Report issued by the Danish Patent Office, dated Feb. 10, 2010, in Appl. No. 200803302-9.
Sinha, S., et al., "Cellular mechanisms of β-amyloid production and secretion" PNAS 96(20):11049-11053 (Sep. 28, 1999).
Sisodia, S.S., "Beta-Amyloid Precursor Protein Cleavage by a Membrane-Bound Protease" PNAS 89(13):6075-6079 (Jul. 1, 1992).
Solomon et al., "Activity of monoclonal antibodies in prevention of in vitro aggregation of their antigens" Stability and Stabilization of Biocatalysts:183-188 (1998).
Solomon et al., "Monoclonal antibodies inhibit in vitro fibrillar aggregation of the Alzheimer B-amyloid peptide" PNAS 93:452-455 (1996).
Solomon, B., et al., "Disaggregation of Alzheimer β-amyloid by site-directed mAb" PNAS 94(8):4109-4112 (Apr. 15, 1997).
Solomon, B., et al., "Vaccination for the prevention and treatment of Alzheimer's disease" Drugs Today [BARC] 36(9):655-663 (Sep. 1, 2000).
Somer, B.G., et al., "Improvement in Sjogren's syndrome following therapy with rituximab for marginal zone lymphoma" Arthritis Rheum 49(3):394-398 (Jun. 15, 2003).
Specks, U., et al., "Response of Wegener's Granulomatosis to anti-CD20 chimeric monoclonal antibody therapy" Arthritis Rheum 44(12):2836-2840 (Dec. 1, 2001).
Spiess, C., et al., "Alternative molecular formats and therapeutic applications for bispecific antibodies" Mol Immunol (Epub: Jan. 27, 2015), 67( Suppl 2 Pt A):95-106 (Oct. 1, 2015).
Stahl, H., et al., "Rituximab in RA: Efficacy and safety from a randomised, controlled trial" Ann Rheum Dis 62( Suppl Suppl 1) ( 2003).
Stasi, R., et al., "Rituximab chimeric anti-CD20 monoclonal antibody treatment for adults with chronic idiopathic thrombocytopenia purpura" Blood 98(4):952-957 (Aug. 15, 2001).

(56) References Cited

OTHER PUBLICATIONS

Stockinger, H., et al. Current Protocols in Immunology "Appendix: Monoclonal Antibodies to Human Cell Surface Antigens" New York, NY—US:John Wiley & Sons, vol. 53(1):A.4A.1-A.4A.49 (May 15, 2003).
Stone, J., et al., "RituximabTherapy for the Induction of Remission and ToleranceIn ANCA-Associated Vasculitis" Clinical Trial Research Summary (Immune Tolerance Network),:1-2 (Sep. 28, 2004) https://web.archive.org/web/20080724222641/http://www.immunetolerance.org/research/autoimmune/trials/stone.html.
Sumbria, R., et al., "Disaggregation of Amyloid Plaque in Brain of Alzheimer's Disease Transgenic Mice with Daily Subcutaneous Administration of a Tetravalent Bispecific Antibody That Targets the Transferrin Receptor and the Abeta Amyloid Peptide" Mol Pharm 10(9):3507-3513 (Sep. 3, 2013).
Supreme People's Court of People's Republic of China Administrative Judgment (2019) Zui Gao Fa Zhi XingZhong No. 235 (The English translation included.).
Tamura et al., "Structural Correlates of an Anticarcinoma Antibody: Identification of Specificity-Determining Residues (SDRs) and Development of a Minimally Immunogenic Antibody Variant by Retention of SDRs Only," J. Immunol., vol. 164, No. 3, pp. 1432-1441, Feb. 2000.
Tedder, T., et al., "The B Cell Surface Molecule B1 is Functionally Linked with B Cell Activation and Differentiation" J Immunol 135(2):973-979 (Aug. 1, 1985).
Tedder, T., et al., "The CD20 Surface Molecule of B Lymphocytes Functions as a Calcium Channel" J Cell Biochem (Abstract #M 023), 14D:195 (1990).
Teeling, J et al., "Characterization of new human CD20 monoclonal antibodies with potent cytolytic activity against non-Hodgkin lymphomas" Blood 104(6):1793-1800 (Sep. 15, 2004).
The Australian Examination Report, mailed on Jun. 23, 2022, in the related Australian Appl. No. 2016333510.
The Brazilian Preliminary Office Action, mailed on Nov. 5, 2020, in the counter-related Brazilian Appl. No. BR112018004733-3.
The Brazilian Preliminary Office Action, mailed on Nov. 5, 2020, in the related Brazilian Appl. No. BR112018004828-3.
The English translation of the Chinese Office Action, mailed on Aug. 3, 2023, in the related Chinese Patent Application No. 202111123164.
The English translation of the Chinese Office Action, dated Jan. 14, 2019, in the related Chinese Appl. No. 2014800782065.5.
The English translation of the Chinese Office Action, mailed on Nov. 3, 2020, in the related Chinese Patent application No. 201680037169.1.
The English translation of the Chinese Office Action, mailed on Feb. 3, 2021, in the related Chinese Appl. No. 201680056850.0.
The English translation of the Chinese Office Action, mailed on Oct. 21, 2022, in the related Chinese Patent Application No. 201480069054.1.
The English translation of the Japanese Office Action, dated Jun. 27, 2023, in the related Japanese Appl. No. 2022-084966.
The English translation of the Russian Office Action, mailed on Mar. 27, 2020, in the related Russian Patent Appl. No. 2018113507/10(021205).
The English translation of the Russian Office Action, dated Mar. 27, 2019, in the related Russian Appl. No. 2016128367/10(044271).
The English translation of the Russian Office Action, dated Jul. 20, 2018, in the related Russian Appl. No. 2016128367/10(044271).
The English translation of the Ukrainian Office Action, mailed on Sep. 9, 2020, in the related Ukrainian Patent application No. a 201800597.
The English translation of the Ukrainian Office Action, mailed on Oct. 28, 2022, in the related Ukrainian Patent Application No. a 2020 07290.
The English translation of the Ukrainian Office Action, mailed on Dec. 13, 2021, in the related Ukrainian Appl. No. a201804776.
The English translation of the Taiwanese Office Action, mailed on May 30, 2024, in the related Taiwanese Appl. No. 112141870.

The European Office Action, mailed on Oct. 12, 2020, in the related European Patent Appl. No. 16 774 687.4.
The extended European Search Report, mailed on Jun. 21, 2021, in the related European Appl. No. 21151524.2.
The New Zealand Office Action, mailed on Jun. 19, 2023, in the related New Zealand Appl. No. 741067.
Thommesen, J., et al., "Lysine 322 in the human IgG3 C(H)2 domain is crucial for antibody dependent complement activation" Mol Immunol 37(16):995-1004 (Nov. 1, 2000).
Thorpe, Monoclonal Antibodies 84: Biological and Clinical Applications A. Pinchera, G. Doria, F. Dammacco & Bargellesi, Editrice Kurtis s.r.l. (Publisher),:475-506 (1985).
Thorpe, P. et al., "The Preparation and Cytotoxic Properties of Antibody-Toxin Conjugates" Immunol Rev 62(1):119-158 (Feb. 1, 1982).
Tobinai et al., "A Review of Obinutuzumab (GA101), a Novel Type II Anti-CD20 Monoclonal Antibody, for the Treatment of Patients with B-Cell Malignancies" Adv Ther 34:324-356 (2017).
Torgov, M., et al., "Generation of an intensely potent anthracycline by a monoclonal antibody—β-galactosidase conjugate" Bioconjugate Chem 16(3):717-21 (May 1, 2005).
Torres, M., et al., "The immunoglobulin constant region contributes to affinity and specificity" Trends Immunol 29(2):91-97 (Feb. 1, 2008).
Tuscano et al., "Successful treatment of Infliximab-refractory rheumatoid arthritis with rituximab" Poster (Presentation #LB11, Poster #444, from OASIS—Online Abstract Submission and Invitation System) Annual Scientific Meeting of the American College of Rheumatology, New Orleans, LA—US, (Oct. 24-29, 2002).
Ulbrich, K., et al., "Transferrin- and transferrin-receptor-antibody-modified nanoparticles enable drug delivery across the blood-brain barrier (BBB)" Eur J Pharm Biopharm 71(2):251-256 (Feb. 1, 2009).
Urlaub, G., et al., "Isolation of chinese hamster cell mutants deficient in dihydrofolate reductase activity" PNAS USA 77(7):4216-4220 (Jul. 1, 1980).
U.S. Appl. No. 19/022,791, filed Jan. 15, 2025, first inventor: Petra Rueger, (U.S. Patent Application is not submitted herewith pursuant to the waiver of 37 C.F.R. § 1.98(a)(2)(iii) issued by the Office on Sep. 21, 2004.).
U.S. Appl. No. 19/022,773, filed Jan. 15, 2025, first inventor: Stefan Dengl. (U.S. Patent Application is not submitted herewith pursuant to the waiver of 37 C.F.R. § 1.98(a)(2)(iii) issued by the Office on Sep. 21, 2004.).
Valentine et al., "B3.9 Structure and function of the B-cell specific 35-37 kDa CD20 protein" Leukocyte Typing III (B-cell antigens—papers), 440-443 (1987).
Valentine, M., et al., "Phosphorylation of the CD20 Phosphoprotein in Resting B Lymphocytes" J Biol Chem 264(19):11282-11287 (Jul. 5, 1989).
Van De Winkel, J.G., et al., "Biology of human immunoglobulin G Fc receptors" J Leukocyte Biol 49(5):511-524 (May 1, 1991).
Van Dijk and Van De Winkel et al., "Human antibodies as next generation therapeutics" Curr Opin Chem Biol 5(4):368-374 (Aug. 2001).
Virgolini, L., et al., "Rituximab in autoimmune diseases" Biomed Pharmacother 58(5):299-309 (Jun. 1, 2004).
Vitetta, E., et al., "Redesigning nature's poisons to create anti-tumor reagents" Science 238(4830):1098-1104 (Nov. 20, 1987).
Vollmers, H., et al., "The 'early birds': Natural IgM antibodies and immune surveillance" Histol Histopathol 20(3):927-937 (Jul. 1, 2005).
Vollmers, H.,, "Death by stress: natural IgM-induced apoptosis" Methods Find Exp Clin Pharmacol 27(3):185-191 (Apr. 1, 2005).
Von Budingen, H., et al., "B cells in multiple sclerosis: connecting the dots" Curr Opin Immunol 23(6):713-720 (Dec. 1, 2011).
Wagner et al., "Modulation of amyloid beta protein precursor processing as a means of retarding progression of Alzheimer's disease" J. Clin. Invest. 104(10):1329-1332 (1999).
Wagner, E., et al., "Transferrin-Polycation Conjugates as Carriers for DNA Uptake Into Cells" PNAS USA 87(9):3410-3414 (May 1, 1990).

(56) References Cited

OTHER PUBLICATIONS

Weide, R., et al., "Successful long-term treatment of systemic lupus erythematosus with rituximab maintenance therapy" Lupus 12(10):779-782 (2003).
Weisser, N., et al., "Applications of single-chain variable fragment antibodies in therapeutics" Biotechnol Adv 27(4):502-520 (Jul. 31, 2009).
Weissmiller, A., et al., "Current advances in using neurotrophic factors to treat neurodegenerative disorders" Transl Neurodegener 1(1):14 (1-9) (Jul. 26, 2012).
Wikipedia et al., "Polysorbate 80-Defined" (Polysorbate 80_Wikipedia_28.03.2011),:1-4 (Mar. 28, 2011).
World Health Organization [WHO] et al., "International Nonproprietary Names for Pharmaceutical Substances (INN)" (Abicipar Pegol; Abiciparum Pegolum), 26(4):401-471 (Dec. 9, 2012).
Wright, A., et al., "Effect of glycosylation on antibody function: Implications for genetic engineering" Trends Biotechnol 15(1):26-32 (Jan. 1, 1997).
Written Opinion of the International Searching Authority PCT/EP2016/073411 dated Dec. 13, 2016.
Wu, G.Y., et al., "Receptor-Mediated in Vitro Gene Transformation by a Soluble DNA Carrier System" J Biol Chem 262(10):4429-4432 (Apr. 5, 1987).
Wylam, M., et al., "Successful treatment of refractory myasthenia gravis using rituximab: a pediatric case report" J Pediatr 143(5):674-677 (Nov. 1, 2003).
Yamane-Ohnuki, N., et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Yan, B., et al., "Soluble expression and target study to brain of anti-TfRScFv" Sheng Wu Gong Cheng Xue Bao [Chinese J Biotechnology] (English Abstract), 20(3):342-347 (May 1, 2004).
Yarilin, "Fundamental Immunology [Osnovi Immunologii]: Textbook." M.: Medicine (Yarilin A.A, Fundamental Immunology [Osnovi Immunologii]: Textbook.—M.: Medicine, 172-174 (1999):172-174.
Yazaki, P. J., et al. Methods in Molecular Biology "Expression of recombinant antibodies in mammalian cell lines" Lo, B.K.C. (ed.), Totowa, NJ:Humana Press, vol. 248:255-268 (2004).
Yu et al., "Boosting Brain Uptake of a Therapeutic Antibody by Reducing Its Affinity for a Transcytosis Target" Science Translational Medicine 3(84):84a44, 8 pages (2011).
Yu, Y.J, et al., "Developing therapeutic antibodies for neurodegenerative disease" Neurotherapeutics 10(3):459-472 (Apr. 3, 2013), 14 pages.
Yu, Y.J., et al., "Therapeutic bispecific antibodies cross the blood-brain barrier in nonhuman primates" Sci Transl Med 6(261):261ra154 (1-11) (Nov. 5, 2014).
Zaja, F., et al., "B-cell depletion with rituximab as treatment for immune hemolytic anemia and chronic thrombocytopenia" Haematologica 87(2):189-195 (Feb. 1, 2002).
Zaja, F., et al., "Efficacy and safety of rituximab in type II mixed cryoglobulinemia" Blood 101(10):3827-3834 (May 15, 2003).
Zaja, F., et al., "Rituximab for myasthenia gravis developing after bone marrow transplant" Neurology 55(7):1062-1063 (Oct. 10, 2000).
Zaja, F., et al., "Rituximab in a case of cold agglutinin disease" Br J Haematol 115(1):232-233 (Oct. 1, 2001).
Zhai et al., "GenBank NCBI) Accesion No. AGB. 75998":1 (Sep. 23, 2021).
Zhai et al., "immunoglobulin heavy chain, partial [Oryctolagus cuniculus]," GenBank: Accession No. AGB75998, Jan. 9, 2013.
Zhang, J. et al., "Design and optimization of a linker for fusion protein construction" Progress in Natural Science 19(10):1197-1200 (2009).
Zhao et al., "Expression, purification and activity analysis of anti-human transferrin receptor scFv" Chinese Journal of Biotechnology (English abstract), 22(3):488-491 (May 1, 2006).
Runzhe, C. et al. (Jun. 2013). "The Application of Transferrin-Transferrin Receptor in the Targeted Therapy of Breast Cancer," Modern Oncology 21(06):1369-1371. (Translation of the Abstract Only).

\* cited by examiner

BISPECIFIC ANTI-HUMAN A-BETA/ANTI-HUMAN TRANSFERRIN RECEPTOR ANTIBODIES

CROSS REFERENCE TO RELATED APPLICATIONS

This application is a continuation of U.S. patent application Ser. No. 18/132,486, filed on Apr. 10, 2023, which is a continuation of U.S. patent application Ser. No. 17/130,477, filed on Dec. 22, 2020, now issued as U.S. Pat. No. 11,787,868 on Oct. 17, 2023, which is a division of U.S. patent application Ser. No. 15/941,655, filed on Mar. 30, 2018, now issued as U.S. Pat. No. 10,941,205 on Mar. 9, 2021, which is a continuation of International Application No. PCT/EP2016/073411, filed on Sep. 30, 2016, which claims benefit of European Patent Application No. 15188064.8, filed on Oct. 2, 2015. Each of prior mentioned applications are hereby incorporated by reference in their entireties.

FIELD OF THE INVENTION

The present invention relates to bispecific antibodies against human A-beta and human transferrin receptor, methods for their production, pharmaceutical compositions containing these antibodies, and uses thereof.

REFERENCE TO AN ELECTRONIC SEQUENCE LISTING

The contents of the electronic sequence listing (146392070603SEQLIST.xml; Size: 34,485 bytes; and Date of Creation: Mar. 25, 2025) is herein incorporated by reference in its entirety.

BACKGROUND

About 70% of all cases of dementia are due to Alzheimer's disease which is associated with selective damage of brain regions and neural circuits critical for cognition. Alzheimer's disease is characterized by neurofibrillary tangles in particular in pyramidal neurons of the hippocampus and numerous amyloid plaques containing mostly a dense core of amyloid deposits and defused halos.

The extracellular neuritic plaques contain large amounts of a pre-dominantly fibrillar peptide termed "amyloid β", "A-beta", "Aβ4", "β-A4" or "Aβ": see Selkoe, Ann. Rev. Cell Biol. 10 (1994) 373-403: Koo PNAS 96 (1999) 9989-9990: U.S. Pat. No. 4,666,829; Glenner BBRC 12 (1984) 1131). This amyloid is derived from "Alzheimer precursor protein/β-amyloid precursor protein" (APP). APPs are integral membrane glycoproteins (see Sisodia PNAS 89 (1992) 6075) and are endoproteolytically cleaved within the AP sequence by a plasma membrane protease, α-secretase (see Sisodia (1992), Joe. cit.). Furthermore, further secretase activity, in particular β-secretase and γ-secretase activity leads to the extracellular release of amyloid-β (Aβ) comprising either 39 amino acids (Aβ39), 40 amino acids (Aβ 40), 42 amino acids (Aβ 42) or 43 amino acids (Aβ 43) (see Sinha PNAS 96 (1999) 11094-1053; Price, Science 282 (1998) 1078-1083: WO 00/72880 or Hardy, TINS 20 (1997) 154).

It is of note that A-beta has several naturally occurring forms, whereby the human forms are referred to as the above mentioned Aβ39, Aβ40, Aβ41, Aβ42 and Aβ43. The most prominent form, Aβ42, has the amino acid sequence (starting from the N-terminus): DAEFRHDSGYEVHHQKLVF-FAEDVGSNKGAIIGLMVGGVVIA (SEQ ID NO: 05). In Aβ41, Aβ40, Aβ39, the C-terminal amino acids A, IA and VIA are missing, respectively. In the Aβ43-form an additional threonine residue is comprised at the C-terminus of the above depicted sequence.

The time required to nucleate Aβ40 fibrils was shown to be significantly longer than that to nucleate Aβ42 fibrils (see e.g. Lansbury, Jr., P. T. and Harper, J. D., Ann. Rev. Biochem. 66 (1997) 385-407). As reviewed in Wagner (J. Clin. Invest. 104 (1999) 1239-1332) the Aβ42 is more frequently found associated with neuritic plaques and is considered to be more fibrillogenic in vitro. It was also suggested that Aβ42 serves as a "seed" in the nucleation-dependent polymerization of ordered non-crystalline Aβ peptides (see e.g. Jarrett, Cell 93 (1993) 1055-1058). Modified APP processing and/or the generation of extracellular plaques containing proteinaceous depositions are not only known from Alzheimer's pathology but also from subjects suffering from other neurological and/or neurodegenerative disorders. These disorders comprise, inter alia, Down's syndrome, hereditary cerebral hemorrhage with amyloidosis Dutch type, Parkinson's disease, ALS (amyotrophic lateral sclerosis), Creutzfeldt Jacob disease, HIV-related dementia and motor neuropathy.

Until now, only limited medical intervention schemes for amyloid-related diseases have been described. For example, cholinesterase inhibitors like galantamine, rivastigmine or donepezil have been discussed as being beneficial in Alzheimer's patients with only mild to moderate disease. However, also adverse events have been reported due to cholinergic action of these drugs. While these cholinergic-enhancing treatments do produce some symptomatic benefit, therapeutic response is not satisfactory for the majority of patients treated. It has been estimated that significant cognitive improvement occurs in only about 5% of treated patients and there is little evidence that treatment significantly alters the course of this progressive disease.

Consequently, there remains a tremendous clinical need for more effective treatments and in particular those which may arrest or delay progression of the disease. Also NMDA-receptor antagonists, like memantine, have been employed more recently.

However, adverse events have been reported due to the pharmacological activity. Further, such a treatment with these NMDA-receptor antagonists can merely be considered as a symptomatic approach and not a disease-modifying one.

Also immunomodulation approaches for the treatment of amyloid-related disorders have been proposed. WO 99/27944 discloses conjugates that comprise parts of the A-beta peptide and carrier molecules whereby said carrier molecule should enhance an immune response. Another active immunization approach is mentioned in WO 00/72880, wherein also A-beta fragments are employed to induce an immune response.

Also passive immunization approaches with general anti-A-beta antibodies have been proposed in WO 99/27944 or WO 01/62801 and specific humanized antibodies directed against portions of A-beta have been described in WO 02/46237, WO 02/088306 and WO 02/088307. WO 00/77178 describes antibodies binding a transition state adopted by B-amyloid during hydrolysis. WO 03/070760 discloses antibody molecules that recognize two discontinuous amino acid sequences on the A-beta peptide.

WO 2014/033074 relates to blood brain barrier shuttles that bind receptors on the blood brain barrier and methods of using the same. Blood-brain barrier drug delivery of IgG fusion proteins with a transferrin receptor monoclonal antibody have been reported by Pardridge, W. (Exp. Opin. Drug Deliv. 12 (2015) 207-222). Yu, Y. J. et al. (Sci. Translat. Med. 6 (2014) 261ra154-261ra154) reported that therapeutic bispecific antibodies cross the blood-brain barrier in non-human primates. The disaggregation of amyloid plaque in brain of Alzheimer's disease transgenic mice with daily subcutaneous administration of a tetravalent bispecific antibody that targets the transferrin receptor and the abeta amyloid peptide was reported by Sumbria, R. K., et al. (Mol. Pharm. 10 (2013) 3507-3513). Niewoehner, J., et al. (Neuron 81 (2014) 49-609 reported an increased brain penetration and potency of a therapeutic antibody using a monovalent molecular shuttle.

SUMMARY

Herein is reported a bispecific antibody comprising
a) one (full length) antibody comprising two pairs each of a (full length) antibody light chain and a (full length) antibody heavy chain, wherein the binding sites formed by each of the pairs of the (full length) heavy chain and the (full length) light chain specifically bind to a first antigen, and
b) one additional Fab fragment, wherein the additional Fab fragment is fused to the C-terminus of one of the heavy chains of the (full length)
antibody, wherein the binding site of the additional Fab fragment
specifically binds to a second antigen,
wherein each of the (full length) antibody light chains comprises in the constant light chain domain (CL) at position 123 the amino acid residue arginine (instead of the wild-type glutamic acid residue: E123R mutation) and at position 124 the amino acid residue lysine (instead of the wild-type glutamine residue: Q124K mutation) (numbering according to Kabat), wherein each of the (full length) antibody heavy chains comprises in the first constant heavy chain domain (CH1) at position 147 an glutamic acid residue (instead of the wild-type lysine residue: K147E mutation) and at position 213 an glutamic acid residue (instead of the wild-type lysine amino acid residue; K213E mutation) (numbering according to Kabat EU index), wherein the additional Fab fragment specifically binding to the second antigen comprises a domain crossover such that the constant light chain domain (CL) and the constant heavy chain domain 1 (CH1) are replaced by each other, and wherein the first antigen is human A-beta protein and the second antigen is human transferrin receptor.

In one embodiment the additional Fab fragment is fused to the C-terminus of the heavy chain by a peptidic linker.

In one embodiment the N-terminus of the heavy chain variable domain of the Fab fragment is fused to the C-terminus of the full length heavy chain or the C-terminus of the peptidic linker.

In one embodiment
a) the full length heavy chain that is fused to the additional Fab fragments has as C-terminal heavy chain amino acid residues the tripeptide LSP wherein the proline thereof is directly fused to the first amino acid residue of the additional Fab fragment or of the peptidic linker via a peptide bond, and
b) the full length heavy chain that is not fused to the additional Fab fragments has as C-terminal heavy chain amino acid residues the tripeptide LSP, or SPG, or PGK.

In one embodiment the (full length) antibody is
a) a full length antibody of the human subclass IgG1,
b) a full length antibody of the human subclass IgG4,
c) a full length antibody of the human subclass IgG1 with the mutations L234A, L235A and P329G,
d) a full length antibody of the human subclass IgG4 with the mutations S228P, L235E and P329G,
e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain,
f) a full length antibody of the human subclass IgG4 with the mutations S228P, L235E and P329G in both heavy chains and the mutations T366W and S354C in one heavy chain and the mutations T366S, L368A, Y407V and Y349C in the respective other heavy chain,
g) a full length antibody of the human subclass IgG1 with the mutations L234A, L235A, P329G, 1253A, H310A and H435A in both heavy chains and the mutations T366W and S354C in one heavy chain and the mutations T366S, L368A, Y407V and Y349C in the respective other heavy chain, or
h) a full length antibody of the human subclass IgG1 with the mutations L234A, L235A, P329G, M252Y, S254T and T256E in both heavy chains and the mutations T366W and S354C in one heavy chain and the mutations T366S, L368A, Y407V and Y349C in the respective other heavy chain.

In one embodiment the (full length) antibody is
a) a full length antibody of the human subclass IgG1,
b) a full length antibody of the human subclass IgG4,
c) a full length antibody of the human subclass IgG1 with the mutations L234A, L235A and P329G,
d) a full length antibody of the human subclass IgG4 with the mutations S228P, L235E and P329G,
e) a full length antibody of the human subclass IgG1 with the mutations L234A, L235A and P329G in both heavy chains and the mutations i) T366W, and ii) S354C or Y349C, in one heavy chain and the mutations
i) T366S, L368A, and Y407V, and ii) Y349C or S354C, in the respective other heavy chain,
f) a full length antibody of the human subclass IgG4 with the mutations S228P, L235E and P329G in both heavy chains and the mutations i) T366W, and ii) S354C or Y349C, in one heavy chain and the mutations
i) T366S, L368A, and Y407V, and ii) Y349C or S354C, in the respective other heavy chain,
g) a full length antibody of the human subclass IgG1 with the mutations L234A, L235A, P329G, 1253A, H310A and H435A in both heavy chains and the mutations i) T366W, and ii) S354C or Y349C, in one heavy chain and the mutations i) T366S, L368A, and Y407V, and ii) Y349C or S354C, in the respective other heavy chain,
h) a full length antibody of the human subclass IgG1 with the mutations L234A, L235A, P329G, M252Y, S254T and T256E in both heavy chains and the mutations i) T366W, and ii) S354C or Y349C, in one heavy chain and the mutations i) T366S, L368A, and Y407V, and ii) Y349C or S354C, in the respective other heavy chain, or
i) a full length antibody of the human subclass IgG1 with the mutations L234A, L235A, P329G, H310A, H433A and Y436A in both heavy chains and the mutations i) T366W, and ii) S354C or Y349C, in one heavy chain and the mutations i) T366S, L368A, and Y407V, and ii) Y349C or S354C, in the respective other heavy chain.

In one embodiment the additional Fab fragment is fused to the C-terminus of the heavy chain comprising the mutation T366W, or to the C-terminus of the heavy chain comprising the mutations T366S, L368A, and Y407V.

In one embodiment
the full length antibody is of the human subclass IgG1 with the mutations L234A, L235A and P329G in both heavy chains and the mutations T366W and S354C in one heavy chain and the mutations T366S, L368A, Y407V and Y349C in the respective other heavy chain, and the additional Fab fragment is fused to the C-terminus of the heavy chain comprising the mutation T366W, or to the C-terminus of the heavy chain comprising the mutations T366S, L368A, and Y407V.

In one embodiment of all aspects, the human A-beta binding site comprises the VH sequence as in SEQ ID NO: 18, including post-translational modifications of that sequence, and the VL sequence as in SEQ ID NO: 19, including post-translational modifications of that sequence.

In one embodiment of all aspects, the human transferrin receptor binding site comprises the VH sequence as in SEQ ID NO: 20, including post-translational modifications of that sequence, and the VL sequence as in SEQ ID NO: 21, including post-translational modifications of that sequence.

In one embodiment the bispecific antibody comprises
i) a light chain with an amino acid sequence that has a sequence identity to SEQ ID NO: 01 of 70% or more,
ii) a heavy chain with an amino acid sequence that has a sequence identity to SEQ ID NO: 02 of 70% or more,
iii) a light chain with an amino acid sequence that has a sequence identity to SEQ ID NO: 03 of 70% or more, and
iv) a heavy chain Fab fragment with an amino acid sequence that has a sequence identity to SEQ ID NO: 04 of 70% or more,
wherein
SEQ ID NO: 01 has the amino acid sequence DIVLTQSPATLSLSPGERATLSCRASQSVSSSY-LAWYQQKPGQAPRLL IYGASSRATGVPARFSG-SGSGTDFTLTISSLEPEDFATYYCLQIYNMPIT FGQGTKVEIKRTVAAPSVFIFPPSDRKLKSG-TASVVCLLNNFYPREAK VQWKVDNALQSG-NSQESVTEQDSKDSTYSLSSTLTLSKADYE-KHKV YACEVTHQGLSSPVTKSFNRGEC.
SEQ ID NO: 02 has the amino acid sequence QVELVES-GGGLVQPGGSLRLSCAASGFTFSSY AMSWV-RQAPGKGLE WVSAINASGTRTYY ADSVKGR-FTISRDNSKNTLYLQMNSLRAEDTAV YYCAR-GKGNTHKPYGYVRYFDVWGQGTLVTVSSAS-TKGPSVFPLAP SSKSTSGGTAALGCLVEDYF-PEPVTVSWNSGALTSGVHTFPAVLQSS GLYS-LSSVVTVPSSSLGTQTYICNVNHKPSNTKVDEK-VEPKSCDKTHT CPPCPAPELLGGPSVFLFPPKP-KDTLMISRTPEVTCVVVDVSHEDPEV KFNW-YVDGVEVHNAKTKPREEQYNSTYRVVSVLT-VLHQDWLNGKE YKCKVSNKALPAPIEKTISK-AKGQPREPQVCTLPPSRDELTKNQVSLS CAVKG-FYPSDIAVEWESNGQPENNYKTTPPVLDSDGSF-FLVSKLTVD KSRWQQGNVFSCSVMHEALHN-HYTQKSLSLSPG,
SEQ ID NO: 03 has the amino acid sequence AIQLTQSPSSLSASVGDRVTITCRASQSISSYLAW-YQQKPGKAPKLLIY RASTLASGVPSRFSGSGSG-TDFTLTISSLQPEDFATYYCQQNYASSNV DNTF-GGGTKVEIKSSASTKGPSVFPLAPSSKSTSGGT-AALGCLVKDYF PEPVTVSWNSGALTSGVHTFP-AVLQSSGLYSLSSVVTVPSSSLGTQTY ICNVN-HKPSNTKVDKKVEPKSC, and
SEQ ID NO: 04 has the amino acid sequence QSMQESGPGLVKPSQTLSLTCTVSGFSLSSY AMSWIRQHPGKGLEWI GYIWSGGSTDYAS-WAKSRVTISKTSTTVSLKLSSVTAADTAVYYCAR RYGTSYPDYGDASGFDPWGQGTLVTVSSAS-VAAPSVFIFPPSDEQLKS GTASVVCLLNNFY-PREAKVQWKVDNALQSGNSQESVTEQDSKD-STY SLSSTLTLSKADYEKHKVYACEVTHQGLS-SPVTKSFNRGEC.

One aspect as reported herein is a bispecific antibody comprising a (full length) light chain that has the amino acid sequence of SEQ ID NO: 01, a (full length) heavy chain that has the amino acid sequence of SEQ ID NO: 02, a (full length) light chain that has the amino acid sequence of SEQ ID NO: 03, and an antibody Fab fragment comprising the amino acid sequences of SEQ ID NO: 04.

In one embodiment the bispecific antibody is monoclonal.

One aspect as reported herein is an isolated nucleic acid encoding the bispecific antibody as reported herein.

One aspect as reported herein is a host cell comprising the nucleic acid as reported herein encoding the bispecific antibody as reported herein.

One aspect as reported herein is a method of producing a bispecific antibody as reported herein comprising the following steps:
a) culturing the host cell as reported herein so that the bispecific antibody is produced, and
b) recovering the bispecific antibody from the cell or the cultivation medium and thereby producing the bispecific antibody as reported herein.

One aspect as reported herein is an immunoconjugate comprising the bispecific antibody as reported herein and a cytotoxic agent.

One aspect as reported herein is a pharmaceutical formulation comprising the bispecific antibody as reported herein and a pharmaceutically acceptable carrier.

One aspect as reported herein is the antibody as reported herein for use as a medicament.

One aspect as reported herein is the bispecific antibody as reported herein for use in treating Alzheimer's disease.

One aspect as reported herein is the bispecific antibody as reported herein for use in inhibiting/slowing down the formation of plaques in the brain.

One aspect as reported herein is the bispecific antibody as reported herein for use in disintegrating β-amyloid plaques.

One aspect as reported herein is the use of the bispecific antibody as reported herein in the manufacture of a medicament.

In one embodiment the medicament is for the treatment of amyloid disorders.

In one embodiment the medicament for the prevention and/or treatment of a disease associated with amyloidogenesis and/or amyloid-plaque formation. In one embodiment the disease is selected from the group consisting of dementia, Alzheimer's disease, motor neuropathy, Down's syndrome, Creutzfeldt Jacob disease, hereditary cerebral hemorrhage with amyloidosis Dutch type, Parkinson's disease, HIV-related dementia, ALS or neuronal disorders related to aging. In one preferred embodiment the medicament is for treatment of Alzheimer's disease.

In one embodiment the medicament is for inhibiting/slowing down the formation of plaques in the brain. In one embodiment the medicament is for medicament for the disintegration of B-amyloid plaques.

One aspect as reported herein is a method of treating an individual having a disease associated with amyloidogenesis and/or amyloid-plaque formation comprising administering to the individual an effective amount of the bispecific antibody as reported herein.

One aspect as reported herein is a method of treating an individual having Alzheimer's disease comprising administering to the individual an effective amount of the bispecific antibody as reported herein.

One aspect as reported herein is a method for the disintegration of β-amyloid plaques in the brain of an individual comprising administering to the individual an effective amount of the bispecific antibody as reported herein to disintegrate β-amyloid plaques in the brain.

One aspect as reported herein is a method of inhibiting/slowing down the formation of plaques in the brain of an individual comprising administering to the individual an effective amount of the bispecific antibody as reported herein to inhibit/slow down the formation of plaques in the brain.

DETAILED DESCRIPTION OF EMBODIMENTS OF THE INVENTION

The knobs into holes dimerization modules and their use in antibody engineering are described in Carter P.: Ridgway J. B. B.; Presta L. G.: Immunotechnology, Volume 2, Number 1, February 1996, pp. 73-73 . . . . The additional disulfide bridge in the CH3 domain is reported in Merchant, A. M., et al., Nat. Biotechnol. 16 (1998) 677-681.

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

I. Definitions

The "blood-brain-barrier" or "BBB" refers to the physiological barrier between the peripheral circulation and the brain and spinal cord which is formed by tight junctions within the brain capillary endothelial plasma membranes, creating a tight barrier that restricts the transport of molecules into the brain, even very small molecules such as urea (60 Daltons). The BBB within the brain, the blood-spinal-cord barrier within the spinal cord, and the blood-retinal-barrier within the retina are contiguous capillary barriers within the CNS, and are herein collectively referred to an the blood-brain-barrier or BBB. The BBB also encompasses the blood-CSF barrier (choroid plexus) where the barrier is comprised of ependymal cells rather than capillary endothelial cells.

The terms "anti-human A-beta antibody" and "an antibody specifically binding to human A-beta" refer to an antibody that is capable of binding the human A-beta peptide with sufficient affinity such that the antibody is useful as a diagnostic and/or therapeutic agent in targeting A-beta peptide.

It is of note that human A-beta has several naturally occurring forms, whereby the human forms are referred to as Aβ39, Aβ40, Aβ41, Aβ42 and Aβ43. The most prominent form, Aβ42, has the amino acid sequence of SEQ ID NO: 05. In Aβ41, Aβ40, Aβ39, the C-terminal amino acids A, IA and VIA are missing, respectively. In the Aβ43 form an additional threonine residue is comprised at the C-terminus of SEQ ID NO: 05. In one embodiment the human A-beta protein has the amino acid sequence of SEQ ID NO: 05.

Thus, the term also encompasses antibodies that bind to a shortened fragment of the human A-beta polypeptide.

The "central nervous system" or "CNS" refers to the complex of nerve tissues that control bodily function, and includes the brain and spinal cord.

A "blood-brain-barrier receptor" (abbreviated "BBBR" herein) is an extracellular membrane-linked receptor protein expressed on brain endothelial cells which is capable of transporting molecules across the BBB or be used to transport exogenous administrated molecules. Examples of BBBR herein include: transferrin receptor (TfR), insulin receptor, insulin-like growth factor receptor (IGF-R), low density lipoprotein receptors including without limitation low density lipoprotein receptor-related protein 1 (LRP1) and low density lipoprotein receptor-related protein 8 (LRP8), and heparin-binding epidermal growth factor-like growth factor (HB-EGF). One preferred BBBR is transferrin receptor (TfR).

The "transferrin receptor" ("TfR") is a transmembrane glycoprotein (with a molecular weight of about 180,000 Da) composed of two disulphide-bonded sub-units (each of apparent molecular weight of about 90,000 Da) involved in iron uptake in vertebrates. In one embodiment, the TfR as mentioned herein is human TfR comprising the amino acid sequence as in Schneider et al (Nature 311 (1984) 675-678), for example. In one embodiment the human transferrin receptor has the amino acid sequence of SEQ ID NO: 22.

A "multispecific antibody" denotes an antibody having binding specificities for at least two different epitopes on the same antigen or two different antigens. Exemplary multispecific antibodies may bind both a BBBR and a brain antigen. Multispecific antibodies can be prepared as full-length antibodies or antibody fragments (e.g. F(ab')$_2$ bispecific antibodies) or combinations thereof (e.g. full length antibody plus additional scFv or Fab fragments). Engineered antibodies with two, three or more (e.g. four) functional antigen binding sites have also been reported (see, e.g., US 2002/0004587 A1).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, including those described herein.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" herein is used in the broadest sense and encompasses various antibody structures, including but not limited to monoclonal antibodies, polyclonal antibodies, and multispecific antibodies (e.g., bispecific antibodies) so long as they exhibit the desired antigen-binding activity.

The term "antibody-dependent cellular cytotoxicity (ADCC)" is a function mediated by Fc receptor binding and refers to lysis of target cells by an antibody as reported herein in the presence of effector cells. ADCC is measured in one embodiment by the treatment of a preparation of CD19 expressing erythroid cells (e.g. K562 cells expressing recombinant human CD19) with an antibody as reported herein in the presence of effector cells such as freshly isolated PBMC (peripheral blood mononuclear cells) or purified effector cells from buffy coats, like monocytes or NK (natural killer) cells. Target cells are labeled with 51Cr and subsequently incubated with the antibody. The labeled cells are incubated with effector cells and the supernatant is analyzed for released 51Cr. Controls include the incubation of the target endothelial cells with effector cells but without the antibody. The capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA). In one preferred embodiment binding to FcγR on NK cells is measured.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$: diabodies: linear antibodies: single-chain antibody molecules (e.g. scFv); and multispecific antibodies formed from antibody fragments. The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$ $Re^{188}$, $Sm^{153}$, $Bi^{212}$, $P^{32}$, $Pb^{212}$ and radioactive isotopes of Lu): chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents): growth inhibitory agents: enzymes and fragments thereof such as nucleolytic enzymes: antibiotics: toxins such as small molecule toxins or enzymatically active toxins of bacterial, fungal, plant or animal origin, including fragments and/or variants thereof; and the various antitumor or anti-cancer agents disclosed below.

The term "complement-dependent cytotoxicity (CDC)" refers to lysis of cells induced by the antibody as reported herein in the presence of complement. CDC is measured in one embodiment by the treatment of CD19 expressing human endothelial cells with an antibody as reported herein in the presence of complement. The cells are in one embodiment labeled with calcein. CDC is found if the antibody induces lysis of 20% or more of the target cells at a concentration of 30 μg/ml. Binding to the complement factor C1q can be measured in an ELISA. In such an assay in principle an ELISA plate is coated with concentration ranges of the antibody, to which purified human C1q or human serum is added. C1q binding is detected by an antibody directed against C1q followed by a peroxidase-labeled conjugate. Detection of binding (maximal binding Bmax) is measured as optical density at 405 nm (OD405) for peroxidase substrate ABTSR (2,2'-azino-di-[3-ethylbenzthiazoline-6-sulfonate (6)]).

"Effector functions" refer to those biological activities attributable to the Fc region of an antibody, which vary with the antibody class. Examples of antibody effector functions include: C1q binding and complement dependent cytotoxicity (CDC): Fc receptor binding: antibody-dependent cell-mediated cytotoxicity (ADCC): phagocytosis: down regulation of cell surface receptors (e.g. B cell receptor); and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J.P., Annu. Rev. Immunol. 9 (1991) 457-492: Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human $IgG_1$ for Fc receptors, the above mentioned mutation sites and methods for measuring binding to FcγRI and FcγRIIA are described in Shields, R. L., et al. J. Biol. Chem. 276 (2001) 6591-6604.

An "effective amount" of an agent, e.g., a pharmaceutical formulation, refers to an amount effective, at dosages and for periods of time necessary, to achieve the desired therapeutic or prophylactic result.

The term "Fc receptor" as used herein refers to activation receptors characterized by the presence of a cytoplasmatic ITAM sequence associated with the receptor (see e.g. Ravetch, J. V. and Bolland, S., Annu. Rev. Immunol. 19 (2001) 275-290). Such receptors are FcγRI, FcγRIIA and FcγRIIIA. The term "no binding of FcγR" denotes that at an antibody concentration of 10 μg/ml the binding of an antibody as reported herein to NK cells is 10% or less of the binding found for anti-OX40L antibody LC.001 as reported in WO 2006/029879.

While $IgG_4$ shows reduced FcR binding, antibodies of other IgG subclasses show strong binding. However Pro238, Asp265, Asp270, Asn297 (loss of Fc carbohydrate), Pro329 and 234, 235, 236 and 237 Ile253, Ser254, Lys288, Thr307, Gln311, Asn434, and His435 are residues which provide if altered also reduce FcR binding (Shields, R. L., et al. J. Biol. Chem. 276 (2001) 6591-6604; Lund, J., et al., FASEB J. 9 (1995) 115-119: Morgan, A., et al., Immunology 86 (1995) 319-324; and EP 0 307 434). In one embodiment the antibody as reported herein is of $IgG_1$ or $IgG_2$ subclass and comprises the mutation PVA236, GLPSS331, and/or L234A/L235A. In one embodiment the antibody as reported herein is of $IgG_4$ subclass and comprises the mutation L235E. In one embodiment the antibody further comprises the mutation S228P.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat, E. A. et al., Sequences of Proteins of Immunological Interest, 5th ed., Public Health Service, National Institutes of Health, Bethesda, MD (1991), NIH Publication 91-3242.

The antibodies as reported herein comprise as Fc-region, in one embodiment an Fc-region derived from human origin. In one embodiment the Fc-region comprises all parts of the human constant region. The Fc-region of an antibody is directly involved in complement activation, C1q binding, C3 activation and Fc receptor binding. While the influence of an antibody on the complement system is dependent on certain conditions, binding to C1q is caused by defined binding sites in the Fc-region. Such binding sites are known in the state of the art and described e.g. by Lukas, T. J., et al., J. Immunol. 127 (1981) 2555-2560; Brunhouse, R., and Cebra, J.J., Mol. Immunol. 16 (1979) 907-917: Burton, D. R., et al., Nature 288 (1980) 338-344: Thommesen, J. E., et al., Mol. Immunol. 37 (2000) 995-1004: Idusogie, E. E., et al., J. Immunol. 164 (2000) 4178-4184; Hezareh, M., et al., J. Virol. 75 (2001) 12161-12168: Morgan, A., et al., Immunology 86 (1995) 319-324; and EP 0 307 434. Such binding sites are e.g. L234, L235, D270, N297, E318, K320, K322, P331 and P329 (numbering according to EU index of Kabat: Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, MD (1991), NIH Publication 91-3242). Antibodies of subclass IgG1, IgG2 and IgG3 usually show complement activation, C1q binding and C3 activation, whereas IgG4 do not activate the complement system, do not bind C1q and do not activate C3. An "Fc-region of an antibody" is a term well known to the skilled artisan and defined on the basis of papain cleavage of antibodies. In one embodiment the Fc-region is a human Fc-region. In one embodiment the Fc-region is of the human IgG4 subclass comprising the mutations S228P and/or L235E (numbering according to EU index of Kabat). In one embodiment the Fc-region is of the human IgG1 subclass comprising the mutations L234A and L235A (numbering according to EU index of Kabat).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1 (L1)-FR2-H2 (L2)-FR3-H3 (L3)-FR4.

The terms "full length antibody", "intact antibody," and "whole antibody" are used herein interchangeably to refer to an antibody having a structure substantially similar to a native antibody structure or having heavy chains that contain an Fc region as defined herein. A "full length antibody" is an antibody that comprises a light and heavy chain antigen-binding variable region (VL, VH) as well as a light chain constant domain (CL) and heavy chain constant domains, CH1, CH2 and CH3. The constant domains may be native sequence constant domains (e.g. human native sequence constant domains) or amino acid sequence variants thereof. In more detail a full length antibody comprises two antibody light chains (each comprising a light chain variable domain and a light chain constant domain) and two antibody heavy chains (each comprising a heavy chain variable domain, a hinge region and the heavy chain constant domains CH1, CH2 and CH3). The C-terminal amino acid residues K or GK may be present or not independently of each other in the two antibody heavy chains of a full length antibody. Also a full length antibody may comprise amino acid additions, mutations and deletions within the domains but not the deletion of an entire domain.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda MD (1991), NIH Publication 91-3242, Vols. 1-3. In one embodiment, for the VL, the subgroup is subgroup kappa I as in Kabat et al . . . supra. In one embodiment, for the VH, the subgroup is subgroup III as in Kabat et al . . . supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs: three in the VH (H1, H2, H3), and three in the VL (L1, L2, L3). HVRs include (a) hypervariable loops occurring at amino acid residues 26-32 (L1), 50-52 (L2), 91-96 (L3), 26-32 (H1), 53-55 (H2), and 96-101 (H3) (Chothia, C. and Lesk, A.M., J. Mol. Biol. 196 (1987) 901-917);

(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, MD (1991), NIH Publication 91-3242.);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262:732-745 (1996)); and (d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al . . . supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-human A-beta/human transferrin receptor antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), whereby between the first and the second constant domain a hinge region is located. Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino 30 acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies as reported herein are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

In one aspect, the invention is based, in part, on the finding that the bispecific anti-human A-beta/human transferrin receptor antibody as reported herein has improved properties. In certain embodiments, bispecific anti-human A-beta/human transferrin receptor antibodies are provided. Antibodies as reported herein are useful, e.g., for the diagnosis or treatment of Alzheimer's disease.

A. Exemplary Bispecific Anti-Human A-Beta/Human Transferrin Receptor Antibodies

In one aspect, the invention provides isolated bispecific antibodies that bind to human A-beta and human transferrin receptor. The antibodies are bispecific antibodies consisting of a full length core antibody and a fused Fab fragment in which certain domains are crosswise exchanged. Thus, the resulting bispecific antibody is asymmetric. Therefore, the bispecific antibody is produced using the heterodimerization technology called knobs-into-holes using a first heavy chain with the so-called knob mutations (HCknob) and a second heavy chain with the so-called hole mutations (HChole).

Antibody 0012, which is also an aspect of the current invention, is composed of four polypeptides that have the amino acid sequence of SEQ ID NO: 06 to 09.

Antibody 0012 is a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein each of the full length antibody light chains comprises in the constant light chain domain (CL) at position 123 the amino acid residue arginine (instead of the wild-type glutamic acid residue: E123R mutation) and at position 124 the amino acid residue lysine (instead of the wild-type glutamine residue: Q124K mutation) (numbering according to Kabat), wherein each of the full length antibody heavy chains comprises in the first constant heavy chain domain (CH1) at position 147 an glutamic acid residue (instead of the wild-type lysine residue: K147E mutation) and at position 213 an glutamic acid residue (instead of the wild-type lysine amino acid residue: K213E mutation) (numbering according to Kabat EU index), wherein the additional Fab fragment specifically binding to the second antigen comprises a domain crossover such that the light chain variable domain (VL) and the heavy chain variable domain (VH) are replaced by each other, and wherein the first antigen is human A-beta protein and the second antigen is human transferrin receptor.

Antibody 0015, which is also an aspect of the current invention, is composed of four polypeptides that have the amino acid sequence of SEQ ID NO: 01 to 03 and SEQ ID NO: 10.

Antibody 0015 is a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein each of the full length antibody light chains comprises in the constant light chain domain (CL) at position 123 the amino acid residue arginine (instead of the wild-type glutamic acid residue: E123R mutation) and at position 124 the amino acid residue lysine (instead of the wild-type glutamine residue: Q124K mutation) (numbering according to Kabat), wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index), wherein the additional Fab fragment specifically binding to the second antigen comprises a domain crossover such that the constant light chain domain (CL) and the constant heavy chain domain 1 (CH1) are replaced by each other, and wherein the first antigen is human A-beta protein and the second antigen is human transferrin receptor.

Antibody 0020, which is also an aspect of the current invention, is composed of three polypeptides that have the amino acid sequence of SEQ ID NO: 11 to 13.

Antibody 0020 is a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein each of the full length antibody light chains comprises in the constant light chain domain (CL) at position 123 the amino acid residue arginine (instead of the wild-type glutamic acid residue: E123R mutation) and at position 124 the amino acid residue lysine (instead of the wild-type glutamine residue: Q124K mutation) (numbering according to Kabat), wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue: K213E mutation) (numbering according to Kabat EU index), wherein the additional Fab fragment specifically binding to the second antigen is a single chain Fab fragment, and wherein the first antigen is human A-beta protein and the second antigen is human transferrin receptor.

Antibody 0024, which is also an aspect of the current invention, is composed of four polypeptides that have the amino acid sequence of SEQ ID NO: 14 to 17.

Antibody 0024 is a bispecific antibody comprising a) one full length antibody comprising two pairs each of a full length antibody light chain and a full length antibody heavy chain, wherein the binding sites formed by each of the pairs of the full length heavy chain and the full length light chain specifically bind to a first antigen, and b) one additional Fab fragment, wherein the additional Fab fragment is fused to the C-terminus of one heavy chain of the full length antibody, wherein the binding site of the additional Fab fragment specifically binds to a second antigen, wherein the additional Fab fragment specifically binding to the second antigen comprises a domain crossover such that the constant light chain domain (CL) and the constant heavy chain domain 1 (CH1) are replaced by each other, and wherein the first antigen is human A-beta protein and the second antigen is human transferrin receptor.

Different allocation/combination of the respective polypeptides on different expression plasmids and different ratios of the resulting plasmids have been used for the recombinant production of the bispecific antibodies. The results are presented in the following Table.

| antibody | plasmid ratio | relative peak area [%] (CE-SDS; non-reduced analysis) | | | |
|---|---|---|---|---|---|
| | | LC | ½ mAb hole | hole-hole chain dimer | antibody monomer |
| 0012 | 1(HChole + LC): 3(HCknob + LCcross) | | 12 | 9 | 78 |
| 0012 | 1(LC): 1(HChole + LC): 3(HCknob + LCcross) | 1 | 9 | 9 | 79 |
| 0012 | 1(LC + HChole): 3(Hcknob + LC): 1(LCcross) | 6 | 9 | 9 | 75 |
| 0015 | 1(HChole + LC): 3(HCknob + LCcross | | 7 | 23 | 62 |
| 0015 | 1(LC): 1(HChole + LC): 3(HCknob + LCcross) | | 4 | 17 | 75 |
| 0015 | 1(LC + HChole): 3(Hcknob + LC): 1(LCcross) | | 4 | 20 | 66 |
| 0020 | 1(HChole + LC): 4(HCknob + LCcross) | | 16 | 11 | 72 |

The bispecific antibodies have been produced in small scale and the by-product distribution has been analyzed after a first purification step using a protein A affinity chromatography and after the second purification step using a preparative size-exclusion chromatography. The results are presented in the following Table.

| antibody | plasmid ratio | harvest 3 liter fermentation after preparative protein A product monomer (CE-SDS not red./yield) | by-product distribution (CE-SDS not red.) | | |
|---|---|---|---|---|---|
| | | | LC | ½ mAb hole | hole-hole dimer + ¾ mAb |
| 0012 | 1:1:3 | 65% 13.3 mg | 3% | 28% | 3.5% |
| 0024 | 1:1:3 | 70% 14.8 mg | 6% | 15% | 7% |
| 0015 | 1:1:3 | 85% 15.8 mg | 4% | 5% | 5% |
| 0020 | 1:4 | 29% 6 mg | 11% | 44% | 8% |

| antibody | plasmid ratio | harvest 3 liter fermentation after preparative protein A and preparative SEC product monomer (CE-SDS not red./yield) | by-product distribution (CE-SDS not red.) | | |
|---|---|---|---|---|---|
| | | | LC | ½ mAb hole | hole-hole dimer + ¾ mAb |
| 0012 | 1:1:3 | >90% 2.8 mg | 5% | 3% | 2.5% |
| 0024 | 1:1:3 | 78% 4 mg | 11% | 5% | 6% |
| 0015 | 1:1:3 | >95% 5.8 mg | 1% | 0.5% | 1% |
| 0020 | 1:4 | 68% 0.8 mg | 13% | 10% | 8.6% |

| antibody | plasmid ratio | harvest 3l after preparative protein A purification monomer by SEC | by-products SEC [%] | | end product by SEC | by-products SEC [%] | |
|---|---|---|---|---|---|---|---|
| | | | HMW | LMW | | HMW | LMW |
| 0012 | 1:1:3 | 78% | 0 | 22 | 97.5% | 0 | 2.5 |
| 0024 | 1:1:3 | 80% | 0 | 20 | 96% | 0 | 4 |
| 0015 | 1:1:3 | 87% | 0 | 13 | 97% | 0 | 3 |
| 0020 | 1:4 | 53% | 7 | 40 | 97% | 0 | 3 |

The anti-A-beta binding site comprises an additional glycosylation site. Therefore the glycosylation has been determined. The results are presented in the following Table.

| antibody | plasmid ratio | HChole CE-SDS; reduced; | | HCknob rel. peak area [%] | |
|---|---|---|---|---|---|
| | | non-glyc. | glyc. | non-glyc. | glyc. |
| 0012 | 1(HChole + LC): 3(HCknob + LCcross) | 10 | 14 | 8 | 18 |
| 0012 | 1(LC): 1(HChole+LC): 3(HCknob + LCcross) | 9 | 13 | 8 | 21 |

-continued

| antibody | plasmid ratio | HChole CE-SDS; reduced; non-glyc. | glyc. | HCknob rel. peak area [%] non-glyc. | glyc. |
|---|---|---|---|---|---|
| 0012 | 1(LC + HChole): 3(Hcknob + LC): 1(LCcross) | 10 | 13 | 7 | 18 |
| 0015 | 1(HChole + LC): 3(HCknob + LCcross) | 7 | 16 | 5 | 25 |
| 0015 | 1(LC): 1(HChole + LC): 3(HCknob + LCcross) | 6 | 16 | 5 | 29 |
| 0015 | 1(LC + HChole): 3(Hcknob + LC): 1(LCcross) | 7 | 15 | 6 | 26 |
| 0020 | 1(HChole + LC): 4(HCknob + LCcross) | 9 | 18 | 7 | 21 |

Percentage of non-glycosylated Fab in 3 liter fermentations after ProtA purification

| antibody | plasmid ratio | HChole CE-SDS; reduced non-glyc. | glyc. | HCknob CE-SDS; reduced non-glyc. | glyc. |
|---|---|---|---|---|---|
| 0012 | 1(LC):1(HChole + LC): 3(HCknob + LCcross) | 23 | 77 | 10 | 90 |
| 0015 | 1(LC): 1(HChole + LC): 3(HCknob + LCcross) | 16 | 84 | 8 | 92 |
| 0024 | 1(LC): 1(HChole + LC): 3(HCknob + LCcross) | 16 | 84 | 7.5 | 92.5 |

Percentage of non-glycosylated Fab in 3l fermentations after ProtA+SEC purification

| antibody | plasmid ratio | HChole CE-SDS; reduced non-glyc. | glyc. | HCknob CE-SDS; reduced non-glyc. | glyc. |
|---|---|---|---|---|---|
| 0012 | 1(LC): 1(HChole + LC): 3(HCknob + LCcross) | 8 | 92 | 6 | 94 |
| 0015 | 1(LC): 1(HChole + LC): 3(HCknob + LCcross) | 10 | 90 | 4.5 | 95.5 |
| 0024 | 1(LC): 1(HChole + LC): 3(HCknob + LCcross) | 8 | 92 | 4.5 | 95.5 |

The stability of the bispecific antibodies has been tested by incubation for 14 day at specific pH values in buffer. The results are presented in the following Table.

| parameter | | antibody 0012 | antibody 0015 | antibody 0024 |
|---|---|---|---|---|
| relative A-beta peptide (1-40) binding by BIAcore | 14 days, pH 6.0, 40° C., His/NaCl buffer | 87% | 96% | 97% |
| | 14 days, pH 7.4, 37° C., PBS buffer | 82% | 86% | 101% |
| relative human transferrin receptor binding by BIAcore | 14 days, pH 6.0, 40° C., His/NaCl buffer | 101% | 91% | 93% |
| | 14 days, pH 7.4, 37° C., PBS buffer | 78% | 85% | 90% |

The aggregation temperature for antibody 0015 and 0024 was determined to be approx. 53-55° C. and for antibody 0012 to be approx. 54-56° C.

The off-rate ($k_d$ in [1/Ms]) for the binding to the human transferrin receptor as determined by BIAcore was comparable for antibodies 0015 and 0024 as well as for the parental anti-human transferrin receptor antibody at 25° C., 37° C. and 40° C.: 1.86E-02 to 1.97E-02, 1.98E-2 to 2.03E-2 and 1.44E-02, respectively.

The A-beta specific effector function of all antibodies were comparable to the parental monospecific anti-A-beta antibody in a U937-cell assay. The data is presented in the following Table.

| antibody | IL-8 [ng/ml] | IP-10 [ng/ml] |
|---|---|---|
| parental anti-A-beta antibody | 5 | 4.3 |
| antibody-0012 | 7 | 5.3 |
| antibody-0015 | — | 5 |
| antibody-0020 | 7 | 4.5 |
| antibody-0024 | 8 | 5.2 |

None of the bispecific antibodies showed neutrophil activation in vitro.

Overall antibody 0015 showed suitable properties and is therefore the preferred aspect of the invention. Furthermore this antibody has improved properties, which lie, amongst others, in the improved side-product profile.

In one aspect herein is provided a bispecific antibody comprising
a) one full length antibody comprising two pairs each of a full length antibody light chain and a full length antibody heavy chain, wherein the binding sites formed by each of the pairs of the full length heavy chain and the full length light chain specifically bind to a first antigen, and
b) one additional Fab fragment, wherein the additional Fab fragment is fused to the C-terminus of one heavy chain of the full length antibody, wherein the binding site of the additional Fab fragment specifically binds to a second antigen,
wherein each of the full length antibody light chains comprises in the constant light chain domain (CL) at position 123 the amino acid residue arginine (instead of the wild-type glutamic acid residue: E123R mutation) and at position 124 the amino acid residue lysine (instead of the wild-type glutamine residue: Q124K mutation) (numbering according to Kabat), wherein each of the full length antibody heavy chains comprises in the first constant heavy chain domain (CH1) at position 147 an glutamic acid residue (instead of the wild-type lysine residue: K147E mutation) and at position 213 an glutamic acid residue (instead of the wild-type lysine amino acid residue: K213E mutation) (numbering according to Kabat EU index), wherein the additional Fab fragment specifically binding to the second antigen comprises a domain crossover such that the constant light chain domain (CL) and the constant heavy chain domain 1 (CH1) are replaced by each other, and wherein the first antigen is human A-beta protein and the second antigen is human transferrin receptor.

Another aspect as reported herein is a bispecific antibody comprising a) one full length antibody comprising two pairs each of a full length antibody light chain and a full length antibody heavy chain, wherein the binding sites formed by each of the pairs of the full length heavy chain and the full length light chain specifically bind to a first antigen, and b) one additional Fab fragment, wherein the additional Fab fragment is fused to the C-terminus of one heavy chain of the full length antibody, wherein the binding site of the additional Fab fragment specifically binds to a second antigen, wherein each of the full length antibody light chains comprises in the constant light chain domain (CL) at position 123 the amino acid residue arginine (instead of the wild-type glutamic acid residue: E123R mutation) and at position 124 the amino acid residue lysine (instead of the wild-type glutamine residue: Q124K mutation) (numbering according to Kabat), wherein each of the full length antibody heavy chains comprises in the first constant heavy chain domain (CH1) at position 147 an glutamic acid residue (instead of the wild-type lysine residue; K147E mutation) and at position 213 an glutamic acid residue (instead of the wild-type lysine amino acid residue; K213E mutation) (numbering according to Kabat EU index), wherein the additional Fab fragment specifically binding to the second antigen comprises a domain crossover such that the constant light chain domain (CL) and the constant heavy chain domain 1 (CH1) are replaced by each other, wherein the first antigen is human A-beta protein and the second antigen is human transferrin receptor, wherein the human A-beta binding site comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 18 and a light chain variable domain (VL) sequence having at least 90%, 91%, 92%, 93%, 94%, 95%, 96%, 97%, 98%, 99%, or 100% sequence identity to the amino acid sequence of SEQ ID NO: 19, and wherein the human transferrin receptor binding site comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 20 and a light chain variable domain (VL) sequence having at least 90%, 91%, 92%, 93%, 94%, 95%, 96%, 97%, 98%, 99%, or 100% sequence identity to the amino acid sequence of SEQ ID NO: 21.

In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but a binding site comprising that sequence retains the ability to bind to its antigen. In certain embodiments, a total of 1 to 10 amino acids have been substituted, inserted and/or deleted in SEQ ID NO: 18 or 20. In certain embodiments, substitutions, insertions, or deletions occur in regions outside the HVRs (i.e., in the FRs).

In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but a binding site comprising that sequence retains the ability to bind to its antigen. In certain embodiments, a total of 1 to 10 amino acids have been substituted, inserted and/or deleted in SEQ ID NO: 19 or 21. In certain embodiments, substitutions, insertions, or deletions occur in regions outside the HVRs (i.e., in the FRs).

In one embodiment, the human A-beta binding site comprises the VH sequence as in SEQ ID NO: 18, including post-translational modifications of that sequence, and the VL sequence as in SEQ ID NO: 19, including post-translational modifications of that sequence.

In one embodiment, the human transferrin receptor binding site comprises the VH sequence as in SEQ ID NO: 20, including post-translational modifications of that sequence, and the VL sequence as in SEQ ID NO: 21, including post-translational modifications of that sequence.

In one embodiment the bispecific antibody comprises
i) a light chain that has a sequence identity to SEQ ID NO: 01 of 70-100%, at least 70%, at least 80%, at least 90%, or 95% or more,
ii) a heavy chain that has a sequence identity to SEQ ID NO: 02 of 70-100%, at least 70%, at least 80%, at least 90%, or 95% or more,
iii) a light chain that has a sequence identity to SEQ ID NO: 03 of 70-100%, at least 70%, at least 80%, at least 90%, or 95% or more, and
iv) a heavy chain Fab fragment that has a sequence identity to SEQ ID NO: 04 of 70-100%, at least 70%, at least 80%, at least 90%, or 95% or more, wherein SEQ ID NO: 01 has the amino acid sequence DIVLTQSPATLSLSPGERATLSCRASQSVSSSY-LAWYQQKPGQAPRLL IYGASSRATGVPARFSG-SGSGTDFTLTISSLEPEDFATYYCLQIYNMPIT FGQGTKVEIKRTVAAPSVFIFPPSDRKLKSGTAS-VVCLLNNFYPREAK VQWKVDNALQSGNSQES-VTEQDSKDSTYSLSSTLTLSKADYEKHKV YACE-VTHQGLSSPVTKSFNRGEC, SEQ ID NO: 02 has the amino acid sequence QVELVES-GGGLVQPGGSLRLSCAASGFTFSSYAMSWVRQ-APGKGLE WVSAINASGTRTYYADSVKGRFTIS-RDNSKNTLYLQMNSLRAEDTAV YYCARGKGN-THKPYGYVRYFDVWGQGTLVTVSSASTKGPS-VFPLAP SSKSTSGGTAALGCLVEDYFPEPVTV-SWNSGALTSGVHTFPAVLQSS GLYSLSSVVTVP-SSSLGTQTYICNVNHKPSNTKVDEKVEPKSCD-KTHT CPPCPAPELLGGPSVFLFPPKPKDTLMIS-RTPEVTCVVVDVSHEDPEV KFNWYVDGVEV-HNAKTKPREEQYNSTYRVVSVLTVLHQDWLN-GKE YKCKVSNKALPAPIEKTISKAKGQPREP-QVCTLPPSRDELTKNQVSLS CAVKGFYPSDIA-VEWESNGQPENNYKTTPPVLDSDGSFFLVSK-LTVD KSRWQQGNVFSCSVMHEALHNHYTQK-SLSLSPG, SEQ ID NO: 03 has the amino acid sequence AIQLTQSPSSLSASVGDRVTITCRASQSISSYLAW-YQQKPGKAPKLLIY RASTLASGVPSRFSGSGSG-TDFTLTISSLQPEDFATYYCQQNYASSNV DNTF-GGGTKVEIKSSASTKGPSVFPLAPSSKSTSGGTA- ALGCLVKDYF PEPVTVSWNSGALTSGVHTFP-
AVLQSSGLYSLSSVVTVPSSSLGTQTY ICNVN-
HKPSNTKVDKKVEPKSC, and SEQ ID NO: 04 has the amino acid sequence QSMQESGPGLVKPSQTLSLTCTVSGFSLSSY AMSWIRQHPGKGLEWI GYIWSGGSTDYAS-WAKSRVTISKTSTTVSLKLSSVTAADTAVYYCAR RYGTSYPDYGDASGFDPWGQGTLVTVSSAS-VAAPSVFIFPPSDEQLKS GTASVVCLLNNFY-PREAKVQWKVDNALQSGNSQESVTEQDSKD-STY SLSSTLTLSKADYEKHKVYACEVTHQGLS-SPVTKSFNRGEC.

Another aspect as reported herein is a bispecific antibody comprising
- a) one full length antibody comprising two pairs each of a full length antibody light chain and a full length antibody heavy chain, wherein the binding sites formed by each of the pairs of the full length heavy chain and the full length light chain specifically bind to a first antigen, and
- b) one additional Fab fragment, wherein the additional Fab fragment is fused to the C-terminus of one heavy chain of the full length antibody, wherein the binding site of the additional Fab fragment specifically binds to a second antigen, wherein each of the full length antibody light chains comprises in the constant light chain domain (CL) at position 123 the amino acid residue arginine (instead of the wild-type glutamic acid residue: E123R mutation) and at position 124 the amino acid residue lysine (instead of the wild-type glutamine residue: Q124K mutation) (numbering according to Kabat), wherein each of the full length antibody heavy chains comprises in the first constant heavy chain domain (CH1) at position 147 an glutamic acid residue (instead of the wild-type lysine residue: K147E mutation) and at position 213 an glutamic acid residue (instead of the wild-type lysine amino acid residue: K213E mutation) (numbering according to Kabat EU index), wherein the additional Fab fragment specifically binding to the second antigen comprises a domain crossover such that the constant light chain domain (CL) and the constant heavy chain domain 1 (CH1) are replaced by each other, wherein the first antigen is human A-beta protein and the second antigen is human transferrin receptor, wherein the human A-beta binding site comprises a heavy chain variable domain (VH) that has the amino acid sequence of SEQ ID NO: 18 and a light chain variable domain (VL) that has the amino acid sequence of SEQ ID NO: 19, and wherein the human transferrin receptor binding site comprises a heavy chain variable domain (VH) that has the amino acid sequence of SEQ ID NO: 20 and a light chain variable domain (VL) that has the amino acid sequence of SEQ ID NO: 21.

Another aspect as reported herein is a bispecific antibody comprising
- a) one full length antibody comprising two pairs each of a full length antibody light chain and a full length antibody heavy chain, wherein the binding sites formed by each of the pairs of the full length heavy chain and the full length light chain specifically bind to a first antigen, wherein the full length antibody comprises an Fc-region that is formed by the Fc-region polypeptides, each comprising the CHI, CH2 and CH3 domain, of the two full length heavy chains, and
- b) one additional Fab fragment, wherein the additional Fab fragment is fused to the C-terminus of one heavy chain of the full length antibody, wherein the binding site of the additional Fab fragment specifically binds to a second antigen, wherein each of the full length antibody light chains comprises in the constant light chain domain (CL) at position 123 the amino acid residue arginine (instead of the wild-type glutamic acid residue; E123R mutation) and at position 124 the amino acid residue lysine (instead of the wild-type glutamine residue: Q124K mutation) (numbering according to Kabat), wherein each of the full length antibody heavy chains comprises in the first constant heavy chain domain (CH1) at position 147 an glutamic acid residue (instead of the wild-type lysine residue: K147E mutation) and at position 213 an glutamic acid residue (instead of the wild-type lysine amino acid residue: K213E mutation) (numbering according to Kabat EU index), wherein the additional Fab fragment specifically binding to the second antigen comprises a domain crossover such that the constant light chain domain (CL) and the constant heavy chain domain 1 (CH1) are replaced by each other, wherein the first antigen is human A-beta protein and the second antigen is human transferrin receptor, wherein the human A-beta binding site comprises a heavy chain variable domain (VH) that has the amino acid sequence of SEQ ID NO: 18 and a light chain variable domain (VL) that has the amino acid sequence of SEQ ID NO: 19, wherein the human transferrin receptor binding site comprises a heavy chain variable domain (VH) that has the amino acid sequence of SEQ ID NO: 20 and a light chain variable domain (VL) that has the amino acid sequence of SEQ ID NO: 21, and wherein the Fc-region polypeptides are
- a) of the human subclass IgG1,
- b) of the human subclass IgG4,
- c) of the human subclass IgG1 with the mutations L234A, L235A and P329G,
- d) of the human subclass IgG4 with the mutations S228P, L235E and P329G,
- e) of the human subclass IgG1 with the mutations L234A, L235A and P329G in both Fc-region polypeptides and the mutations T366W and S354C in one Fc-region polypeptide and the mutations T366S, L368A, Y407V and Y349C in the respective other Fc-region polypeptide,
- f) of the human subclass IgG4 with the mutations S228P and P329G in both Fc-region polypeptides and the mutations T366W and S354C in one Fc-region polypeptide and the mutations T366S, L368A, Y407V and Y349C in the respective other Fc-region polypeptide,
- g) of the human subclass IgG1 with the mutations L234A, L235A, P329G, I253A, H310A and H435A in both Fc-region polypeptides and the mutations T366W and S354C in one Fc-region polypeptide and the mutations T366S, L368A, Y407V and Y349C in the respective other Fc-region polypeptide,
- h) of the human subclass IgG1 with the mutations L234A, L235A, P329G, M252Y, S254T and T256E in both Fc-region polypeptides and the mutations T366W and S354C in one Fc-region polypeptide and the mutations T366S, L368A, Y407V and Y349C in the respective other Fc-region polypeptide, or i) a full length antibody of the human subclass IgG1 with the mutations L234A, L235A, P329G, H310A, H433A and Y436A in both heavy chains and the mutations i) T366W, and ii) S354C or Y349C, in one heavy chain and the mutations i) T366S, L368A, and Y407V, and ii) Y349C or S354C, in the respective other heavy chain.

In a further aspect, a bispecific anti-human A-beta/human transferrin receptor antibody according to any of the above embodiments may incorporate any of the features, singly or in combination, as described in Sections 1-3 below:

1. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al . . . Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs. (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing specificity determining region (SDR) grafting): Padlan, E.A., Mol. Immunol. 28 (1991) 489-498 (describing "resurfacing"): Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M.J. et al., J. Immunol. 151 (1993) 2296-2308: framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

2. Human Antibodies

In certain embodiments, an antibody provided herein is a human antibody. Human antibodies can be produced using various techniques known in the art. Human antibodies are described generally in van Dijk, M.A. and van de Winkel, J.G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology: U.S. Pat. No. 5,770,429 describing HUMABR technology: U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95) Human antibodies generated via human B-cell hybridoma technology are also described in Li, J. et al., Proc Natl. Acad. Sci USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

3. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in the Table below under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile:
(2) neutral hydrophilic: Cys, Ser, Thr, Asn, Gln:
(3) acidic: Asp, Glu:
(4) basic: His, Lys, Arg:
(5) residues that influence chain orientation: Gly, Pro:
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P.S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J.A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright, A. and Morrison, S.L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody as reported herein may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about +3 amino acids upstream or downstream of position 297, i.e., between positions 294 and 300, due to minor sequence variations in antibodies. Such fucosylation variants may have improved ADCC function. See, e.g., US 2003/0157108: US 2004/0093621. Examples of publications related to "defucosylated" or "fucose-deficient" antibody variants include: US 2003/0157108: WO 2000/61739: WO 2001/29246: US 2003/0115614: US 2002/0164328: US 2004/0093621: US 2004/0132140: US 2004/0110704: US 2004/0110282: US 2004/0109865: WO 2003/085119: WO 2003/084570: WO 2005/035586: WO 2005/035778: WO 2005/053742: WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545: US 2003/0157108; and WO 2004/056312, especially at Example 11), and knockout cell lines, such as alpha-1,6-fucosyltransferase gene, FUT8. knockout CHO cells (see, e.g., Yamane-Ohnuki, N. et al., Biotech. Bioeng. 87 (2004) 614-622: Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878: U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087: WO 1998/58964; and WO 1999/22764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, herein is contemplated an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J.P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502): U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes. R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171: Cragg, M.S. et al., Blood 101 (2003) 1045-1052; and Cragg, M.S. and M.J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006:1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan, A.R. and Winter, G., Nature 322 (1988) 738-740: U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain: A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding a bispecific anti-human A-beta/human transferrin receptor antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20 cell). In one embodiment, a method of making a bispecific anti-human A-beta/human transferrin receptor antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of a bispecific anti-human A-beta/human transferrin receptor antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K.A., In: Methods in Molecular Biology, Vol. 248, Lo, B.K.C. (ed.), Humana Press, Totowa, NJ (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T.U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7): human embryonic kidney line (293 or 293 cells as described, e.g., in Graham, F.L. et al., J. Gen Virol. 36 (1977) 59-74): baby hamster kidney cells (BHK): mouse sertoli cells (TM4 cells as described, e.g., in Mather, J.P., Biol. Reprod. 23 (1980) 243-252): monkey kidney cells (CV1): African green monkey kidney cells (VERO-76): human cervical carcinoma cells (HELA): canine kidney cells (MDCK: buffalo rat liver cells (BRL 3A): human lung cells (W138): human liver cells (Hep G2);

mouse mammary tumor (MMT 060562): TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR CHO cells (Urlaub, G. et al., Proc. Natl. Acad. Sci. USA 77 (1980) 4216-4220); and myeloma cell lines such as YO, NSO and Sp2/0. For a review of certain mammalian host cell lines suitable for antibody production, see, e.g., Yazaki, P. and Wu, A.M., Methods in Molecular Biology, Vol. 248, Lo, B.K.C. (ed.), Humana Press, Totowa, NJ (2004), pp. 255-268.

C. Methods and Compositions for Diagnostics and Detection

In certain embodiments, any of the bispecific anti-human A-beta/human transferrin receptor antibodies provided herein are useful for detecting the presence of A-beta in a biological sample. The term "detecting" as used herein encompasses quantitative or qualitative detection. In certain embodiments, a biological sample comprises a cell or tissue.

In one embodiment, a bispecific anti-human A-beta/human transferrin receptor antibody for use in a method of diagnosis or detection is provided. In a further aspect, a method of detecting the presence of A-beta in a biological sample is provided. In certain embodiments, the method comprises contacting the biological sample with a bispecific anti-human A-beta/human transferrin receptor antibody as described herein under conditions permissive for binding of the bispecific anti-human A-beta/human transferrin receptor antibody to A-beta, and detecting whether a complex is formed between the bispecific anti-human A-beta/human transferrin receptor antibody and A-beta. Such method may be an in vitro or in vivo method.

In certain embodiments, labeled bispecific anti-human A-beta/human transferrin receptor antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, ruceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

D. Pharmaceutical Formulations

Pharmaceutical formulations of a bispecific anti-human A-beta/human transferrin receptor antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids: antioxidants including ascorbic acid and methionine: preservatives (such as octadecyl dimethylbenzyl ammonium chloride: hexamethonium chloride: benzalkonium chloride: benzethonium chloride: phenol, butyl or benzyl alcohol: alkyl parabens such as methyl or propyl paraben: catechol: resorcinol: cyclohexanol: 3-pentanol; and m-cresol): low molecular weight (less than about 10 residues) polypeptides: proteins, such as serum albumin, gelatin, or immunoglobulins: hydrophilic polymers such as poly(vinylpyrrolidone): amino acids such as glycine, glutamine, asparagine, histidine, arginine, or lysine: monosaccharides, disaccharides, and other carbohydrates including glucose, mannose, or dextrins: chelating agents such as EDTA: sugars such as sucrose, mannitol, trehalose or sorbitol: salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, 20) Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxy butyric acid.

The formulations to be used for in vivo administration are generally sterile. Sterility may be readily accomplished, e.g., by filtration through sterile filtration membranes. In one embodiment the formulation is isotonic.

E. Therapeutic Methods and Compositions

Any of the bispecific anti-human A-beta/human transferrin receptor antibodies provided herein may be used in therapeutic methods.

In one aspect, a bispecific anti-human A-beta/human transferrin receptor antibody for use as a medicament is provided. In further aspects, a bispecific anti-human A-beta/human transferrin receptor antibody for use in preventing and/or treating a disease associated with amyloidogenesis and/or amyloid-plaque formation is provided. In certain embodiments, a bispecific anti-human A-beta/human transferrin receptor antibody for use in a method of treatment is provided. In certain embodiments, herein is provided a bispecific anti-human A-beta/human transferrin receptor antibody for use in a method of treating an individual having a disease associated with amyloidogenesis and/or amyloid-plaque formation comprising administering to the individual an effective amount of the bispecific anti-human A-beta/human transferrin receptor antibody. In one such embodiment, the method further comprises administering to the individual an effective amount of at least one additional therapeutic agent, such as listed below or an anti-pTau or an anti-alpha-synuclein antibody. In further embodiments, herein is provided a bispecific anti-human A-beta/human transferrin receptor antibody for use in inhibiting the formation of plaques and/or disintegrating β-amyloid plaques. In certain embodiments, herein is provided a bispecific anti-human A-beta/human transferrin receptor antibody for use in a method of inhibiting the formation of plaques and/or disintegrating B-amyloid plaques in an individual comprising administering to the individual an effective of the bispecific anti-human A-beta/human transferrin receptor antibody to inhibit the formation of plaques and/or to disintegrate B-amyloid plaques. An "individual" according to any of the above embodiments is preferably a human.

In a further aspect, herein is provided the use of a bispecific anti-human A-beta/human transferrin receptor antibody in the manufacture or preparation of a medicament. In one embodiment, the medicament is for treatment of a disease associated with amyloidogenesis and/or amyloid-plaque formation. In a further embodiment, the medicament is for use in a method of treating a disease associated with amyloidogenesis and/or amyloid-plaque formation comprising administering to an individual having a disease associated with amyloidogenesis and/or amyloid-plaque formation an effective amount of the medicament. In one such embodiment, the method further comprises administering to the individual an effective amount of at least one additional therapeutic agent, such as listed below or an anti-pTau or an anti-alpha synuclein antibody. In a further embodiment, the medicament is for the inhibition of the formation of plaques and/or the disintegration of β-amyloid plaques. In a further embodiment, the medicament is for use in a method of inhibiting the formation of plaques and/or the disintegration of β-amyloid plaques in an individual comprising administering to the individual an amount effective of the medicament to inhibit the formation of plaques and/or to disintegrate B-amyloid plaques. An "individual" according to any of the above embodiments may be a human.

In a further aspect, herein is provided a method for treating a disease associated with amyloidogenesis and/or amyloid-plaque formation. In one embodiment, the method comprises administering to an individual having a disease associated with amyloidogenesis and/or amyloid-plaque formation an effective amount of a bispecific anti-human A-beta/human transferrin receptor antibody. In one such embodiment, the method further comprises administering to the individual an effective amount of at least one additional therapeutic agent, such as given below or an anti-pTau or an anti-alpha-synuclein antibody. An "individual" according to any of the above embodiments may be a human.

In a further aspect, herein is provided a method for inhibiting the formation of plaques and/or for disintegrating β-amyloid plaques in an individual. In one embodiment, the method comprises administering to the individual an effective amount of a bispecific anti-human A-beta/human transferrin receptor antibody to inhibit the formation of plaques and/or to disintegrate β-amyloid plaques. In one embodiment, an "individual" is a human.

In a further aspect, herein are provided pharmaceutical formulations comprising any of the bispecific anti-human A-beta/human transferrin receptor antibodies provided herein, e.g., for use in any of the above therapeutic methods. In one embodiment, a pharmaceutical formulation comprises any of the bispecific anti-human A-beta/human transferrin receptor antibodies provided herein and a pharmaceutically acceptable carrier. In another embodiment, a pharmaceutical formulation comprises any of the bispecific anti-human A-beta/human transferrin receptor antibodies provided herein and at least one additional therapeutic agent, e.g., as given below or an anti-pTau or an anti-alpha-synuclein antibody.

Antibodies as reported herein can be used either alone or in combination with other agents in a therapy. For instance, an antibody as reported herein may be co-administered with at least one additional therapeutic agent. In certain embodiments, an additional therapeutic agent is a therapeutic agent effective to treat the same or a different neurological disorder as the bispecific antibody as reported herein is being employed to treat. Exemplary additional therapeutic agents include, but are not limited to: the various neurological drugs described above, cholinesterase inhibitors (such as donepezil, galantamine, rovastigmine, and tacrine), NMDA receptor antagonists (such as memantine), amyloid beta peptide aggregation inhibitors, antioxidants, γ-secretase modulators, nerve growth factor (NGF) mimics or NGF gene therapy, PPARy agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicrotinic receptor modulators, active or passive amyloid beta peptide immunization, phosphodiesterase inhibitors, serotonin receptor antagonists and anti-amyloid beta peptide antibodies. In certain embodiments, the at least one additional therapeutic agent is selected for its ability to mitigate one or more side effects of the neurological drug.

Such combination therapies noted above encompass combined administration (where two or more therapeutic agents are included in the same or separate formulations), and separate administration, in which case, administration of the antibody as reported herein can occur prior to, simultaneously, and/or following, administration of the additional therapeutic agent or agents. In one embodiment, administration of the bispecific anti-human A-beta/human transferrin receptor antibody and administration of an additional therapeutic agent occur within about one month, or within about one, two or three weeks, or within about one, two, three, four, five, or six days, of each other. Antibodies as reported herein can also be used in combination with other interventional therapies such as, but not limited to, radiation therapy, behavioral therapy, or other therapies known in the art and appropriate for the neurological disorder to be treated or prevented.

An antibody as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

Lipid-based methods of transporting the fusion construct or a compound across the BBB include, but are not limited to, encapsulating the fusion construct or a compound in liposomes that are coupled to monovalent binding entity that bind to receptors on the vascular endothelium of the BBB (see e.g., US 2002/0025313), and coating the monovalent binding entity in low-density lipoprotein particles (see e.g., US 2004/0204354) or apolipoprotein E (see e.g., US 2004/0131692).

For the prevention or treatment of disease, the appropriate dosage of an antibody as reported herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg. 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate as reported herein in place of or in addition to a bispecific anti-human A-beta/human transferrin receptor antibody.

III. Articles of Manufacture

In another aspect as reported herein, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody as reported herein. The label or package insert indicates that the composition is used for treating the condition of choice. Moreover, the article of manufacture may comprise (a) a first container with a composition contained therein, wherein the composition comprises an antibody as reported herein; and (b) a second container with a composition contained therein, wherein the composition comprises a further cytotoxic or otherwise therapeutic agent. The article of manufacture in this embodiment may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate as reported herein in place of or in addition to a bispecific antibody as reported herein.

IV. Examples

The following are examples of methods and compositions of the invention. It is understood that various other embodiments may be practiced, given the general description provided above.

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991). Amino acids of antibody chains are numbered and referred to according to numbering according to Kabat (Kabat, E. A., et al., Sequences of Proteins of Immunological Interest, 5th ed., Public Health Service, National Institutes of Health, Bethesda, MD (1991)).

Recombinant DNA Techniques

Standard methods were used to manipulate DNA as described in Sambrook, J. et al., Molecular Cloning: A laboratory manual: Cold Spring Harbor Laboratory Press, Cold Spring Harbor, New York, 1989. The molecular biological reagents were used according to the manufacturer's instructions.

Gene Synthesis

Desired gene segments were prepared from oligonucleotides made by chemical synthesis. The long gene segments, which were flanked by singular restriction endonuclease cleavage sites, were assembled by annealing and ligating oligonucleotides including PCR amplification and subsequently cloned via the indicated restriction sites. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at MediGenomix GmbH (Martinsried, Germany) or SequiServe GmbH (Vaterstetten, Germany).

DNA and Protein Sequence Analysis and Sequence Data Management

The GCG's (Genetics Computer Group, Madison, Wisconsin) software package version 10.2 and Infomax's Vector NTI Advance suite version 8.0 was used for sequence creation, mapping, analysis, annotation and illustration.

Expression Vectors

For the expression of the described bispecific antibodies, expression plasmids for transient expression (e.g. in HEK293 cells) based either on a cDNA organization with or without a CMV-intron A promoter or on a genomic organization with a CMV promoter can be applied.

Beside the antibody expression cassette the vectors contain:
- an origin of replication which allows replication of this plasmid in E. coli, and
- a β-lactamase gene which confers ampicillin resistance in E. coli.

The transcription unit of the antibody gene is composed of the following elements:
- unique restriction site(s) at the 5' end
- the immediate early enhancer and promoter from the human cytomegalovirus,
- the intron A sequence in the case of cDNA organization,
- a 5'-untranslated region derived from a human antibody gene,
- an immunoglobulin heavy chain signal sequence,
- the respective antibody chain encoding nucleic acid either as cDNA or with genomic exon-intron organization,
- a 3' untranslated region with a polyadenylation signal sequence, and
- unique restriction site(s) at the 3' end.

The fusion genes encoding the antibody chains are generated by PCR and/or gene synthesis and assembled by known recombinant methods and techniques by connection of the according nucleic acid segments e.g. using unique restriction sites in the respective vectors. The subcloned nucleic acid sequences are verified by DNA sequencing. For transient transfections larger quantities of the plasmids are prepared by plasmid preparation from transformed E. coli cultures (Nucleobond AX, Macherey-Nagel).

For all constructs knob-into-hole heterodimerization technology was used with a typical knob (T366W) substitution in the first CH3 domain and the corresponding hole substitutions (T366S, L368A and Y407V) in the second CH3 domain (as well as two additional introduced cysteine residues S354C/Y349'C) (contained in the respective corresponding heavy chain (HC) sequences depicted above).

Cell Culture Techniques

Standard cell culture techniques as described in Current Protocols in Cell Biology (2000), Bonifacino, J.S., Dasso, M., Harford, J.B., Lippincott-Schwartz, J. and Yamada, K.M. (eds.), John Wiley & Sons, Inc., are used.

Transient Transfections in HEK293-F System

The bispecific antibodies are produced by transient expression. Therefore a transfection with the respective plasmids using the HEK293-F system (Invitrogen) according to the manufacturer's instruction is done. Briefly, HEK293-F cells (Invitrogen) growing in suspension either in a shake flask or in a stirred fermenter in serum-free FreeStyle™ 293 expression medium (Invitrogen) are transfected with a mix of the respective expression plasmids and 293fectin™ or fectin (Invitrogen). For 2 L shake flask (Corning) HEK293-F cells are seeded at a density of $1.0*10^6$ cells/mL in 600 mL and incubated at 120 rpm, 8% CO2. On the next day the cells are transfected at a cell density of approx. $1.5*10^6$ cells/mL with approx. 42 mL of a mixture of A) 20 mL Opti-MEM medium (Invitrogen) comprising 600 μg total plasmid DNA (1 μg/mL) and B) 20 ml Opti-MEM medium supplemented with 1.2 mL 293 fectin or fectin (2 μl/mL). According to the glucose consumption glucose solution is added during the course of the fermentation. The supernatant containing the secreted antibody is harvested after 5-10 days and antibodies are either directly purified from the supernatant or the supernatant is frozen and stored.

Protein Determination

The protein concentration of purified antibodies and derivatives was determined by determining the optical density (OD) at 280 nm, using the molar extinction coefficient calculated on the basis of the amino acid sequence according to Pace, et al., Protein Science 4 (1995) 2411-1423.

Antibody Concentration Determination in Supernatants

The concentration of antibodies and derivatives in cell culture supernatants was estimated by immunoprecipitation with protein A agarose-beads (Roche Diagnostics GmbH, Mannheim, Germany). Therefore, 60 μL protein A Agarose beads were washed three times in TBS-NP40 (50 mM Tris buffer, pH 7.5, supplemented with 150 mM NaCl and 1% Nonidet-P40). Subsequently, 1-15 mL cell culture supernatant was applied to the protein A Agarose beads pre-equilibrated in TBS-NP40. After incubation for at 1 hour at room temperature the beads were washed on an Ultrafree-MC-filter column (Amicon) once with 0.5 mL TBS-NP40, twice with 0.5 mL 2× phosphate buffered saline (2×PBS, Roche Diagnostics GmbH, Mannheim, Germany) and briefly four times with 0.5 mL 100 mM Na-citrate buffer (pH 5.0). Bound antibody was eluted by addition of 35 μl NuPAGE® LDS sample buffer (Invitrogen). Half of the sample was combined with NuPAGE® sample reducing agent or left unreduced, respectively, and heated for 10 min at 70° C. Consequently, 5-30 μl were applied to a 4-12% NuPAGE® Bis-Tris SDS-PAGE gel (Invitrogen) (with MOPS buffer for non-reduced SDS-PAGE and MES buffer with NuPAGER antioxidant running buffer additive (Invitrogen) for reduced SDS-PAGE) and stained with Coomassie Blue.

The concentration of the antibodies in cell culture supernatants was quantitatively measured by affinity HPLC chromatography. Briefly, cell culture supernatants containing antibodies that bind to protein A were applied to an Applied Biosystems Poros A/20 column in 200 mM $KH_2PO_4$, 100 mM sodium citrate, pH 7.4 and eluted with 200 mM NaCl, 100 mM citric acid, pH 2.5 on an Agilent HPLC 1100 system. The eluted antibody was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Streptavidin A-96 well microtiter plates (Roche Diagnostics GmbH, Mannheim, Germany) were coated with 100 μL/well biotinylated anti-human IgG capture molecule F(ab') 2<h-Fcγ> BI (Dianova) at 0.1 μg/mL for 1 hour at room temperature or alternatively overnight at 4° C. and subsequently washed three times with 200 μL/well PBS, 0.05% Tween (PBST, Sigma). Thereafter, 100 μL/well of a dilution series in PBS (Sigma) of the respective antibody containing cell culture supernatants was added to the wells and incubated for 1-2 hour on a shaker at room temperature. The wells were washed three times with 200 μL/well PBST and bound antibody was detected with 100 μl F (ab) 2<hFcγ>POD (Dianova) at 0.1 μg/mL as the detection antibody by incubation for 1-2 hours on a shaker at room temperature. Unbound detection antibody was removed by washing three times with 200 μL/well PBST. The bound detection antibody was detected by addition of 100 μL ABTS/well followed by incubation. Determination of absorbance was performed on a Tecan Fluor Spectrometer at a measurement wavelength of 405 nm (reference wavelength 492 nm).

Preparative Antibody Purification

Antibodies were purified from filtered cell culture supernatants referring to standard protocols. In brief, antibodies were applied to a protein A Sepharose column (GE healthcare) and washed with PBS. Elution of antibodies was achieved at pH 2.8 followed by immediate neutralization. Aggregated protein was separated from monomeric antibodies by size exclusion chromatography (Superdex 200, GE Healthcare) in PBS or in 20 mM Histidine buffer comprising 150 mM NaCl (pH 6.0). Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGER Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGER) antioxidant running buffer additive) or MOPS (non-reduced gels) running buffer was used.

CE-SDS

Purity and antibody integrity were analyzed by CE-SDS using microfluidic Labchip technology (PerkinElmer, USA). Therefore, 5 μl of antibody solution was prepared for CE-SDS analysis using the HT Protein Express Reagent Kit according manufacturer's instructions and analyzed on LabChip GXII system using a HT Protein Express Chip. Data were analyzed using LabChip GX Software.

Analytical Size Exclusion Chromatography

Size exclusion chromatography (SEC) for the determination of the aggregation and oligomeric state of antibodies was performed by HPLC chromatography. Briefly, protein A purified antibodies were applied to a Tosoh TSKgel G3000SW column in 300 mM NaCl, 50 mM $KH_2PO_4$/$K_2HPO_4$ buffer (pH 7.5) on an Dionex Ultimate® system (Thermo Fischer Scientific), or to a Superdex 200 column (GE Healthcare) in 2×PBS on a Dionex HPLC-System. The eluted antibody was quantified by UV absorbance and integration of peak areas. BioRad Gel Filtration Standard 151-1901 served as a standard.

Mass Spectrometry

This section describes the characterization of the bispecific antibodies with emphasis on their correct assembly. The expected primary structures were analyzed by electrospray ionization mass spectrometry (ESI-MS) of the deglycosylated intact antibody and in special cases of the deglycosylated/limited LysC digested antibody.

The antibodies were deglycosylated with N-Glycosidase F in a phosphate or Tris buffer at 37° C. for up to 17 h at a protein concentration of 1 mg/ml. The limited LysC (Roche Diagnostics GmbH, Mannheim, Germany) digestions were performed with 100 μg deglycosylated antibody in a Tris buffer (pH 8) at room temperature for 120 hours, or at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Chemical Degradation Test

Samples were split into three aliquots and re-buffered into 20 mM His/His*HCl, 140 mM NaCl, pH 6.0 or into PBS, respectively, and stored at 40° C. (His/NaCl) or 37° C. (PBS). A control sample was stored at −80° C.

After incubation ended, samples were analyzed for relative active concentration (BIAcore), aggregation (SEC) and fragmentation (capillary electrophoresis or SDS-PAGE) and compared with the untreated control.

Thermal Stability

Samples were prepared at a concentration of 1 mg/mL in 20 mM Histidine/Histidine chloride, 140 mM NaCl, pH 6.0, transferred into an optical 384-well plate by centrifugation through a 0.4 μm filter plate and covered with paraffin oil. The hydrodynamic radius was measured repeatedly by dynamic light scattering on a DynaPro Plate Reader (Wyatt) while the samples were heated with a rate of 0.05° C./min from 25° C. to 80° C.

Alternatively, samples were transferred into a 10 μL micro-cuvette array and static light scattering data as well as fluorescence data upon excitation with a 266 nm laser were recorded with an Optim1000 instrument (Avacta Inc.), while they were heated at a rate of 0.1° C./min from 25° C. to 90° C.

The aggregation onset temperature is defined as the temperature at which the hydrodynamic radius (DLS) or the scattered light intensity (Optim1000) starts to increase.

Alternatively, samples were transferred in a 9 μL multi-cuvette array. The multi-cuvette array was heated from 35° C. to 90° C. at a constant rate of 0.1° C./minute in an Optim1000 instrument (Avacta Analytical Inc.). The instrument continuously records the intensity of scattered light of a 266 nm laser with a data point approximately every 0.5° C. Light scattering intensities were plotted against the temperature. The aggregation onset temperature (T_agg) is defined as the temperature at which the scattered light intensity begins to increase.

The melting temperature is defined as the inflection point in fluorescence intensity vs. wavelength graph

Example 1

Expression and Purification

The bispecific antibodies were produced as described above in the general materials and methods section.

The bispecific antibodies were purified from the supernatant by a combination of protein A affinity chromatography and size exclusion chromatography. The obtained products were characterized for identity by mass spectrometry and analytical properties such as purity by CE-SDS, monomer content and stability.

The expected primary structures were analyzed by electrospray ionization mass spectrometry (ESI-MS) of the deglycosylated intact antibody and deglycosylated/plasmin digested or alternatively deglycosylated/limited LysC digested antibody as described in the general methods section.

Additional analytical methods (e.g. thermal stability, mass spectrometry and functional assessment) were only applied after protein A and SEC purification.

Example 2

Determination of Binding to Aβ1-40 Fibers In Vitro by ELISA

Binding of the bispecific antibodies to fibrillar Aβ is measured by an ELISA assay. Briefly, Aβ(1-40) is coated at 7 μg/mL in PBS onto Maxisorb plates for 3 days at 37° C. to produce fibrillar Abeta, and then dried for 3 h at RT. The plate is blocked with 1% CroteinC and 0.1% RSA in PBS (blocking buffer) for 1 h at RT, then washed once with wash buffer. Bispecific antibodies or controls are added at concentrations up to 100 nM in blocking buffer and incubated at 4° C. overnight. After 4 wash steps, constructs are detected by addition of anti-human-IgG-HRP (Jackson Immunoresearch) at 1:10,000 dilution in blocking buffer (1 RT), followed by 6 washes and incubation in TMB (Sigma). Absorbance is read out at 450 nm after stopping color development with 1 N HCl.

Example 3

Determination of Binding to Transferrin Receptor In Vitro

Binding of the bispecific antibodies to murine transferrin receptor is tested by FACS analysis on mouse X63.AG8-563 myeloma cells. If the AB antibody shows a certain tendency to non-specifically bind to Ag8 cells, specific binding can be quantified by co-incubation with a 20fold excess of anti-mouse-TfR antibody. Cells are harvested by centrifugation, washed once with PBS and $5 \times 10^4$ cells incubated with a 1.5 pM to 10 nM dilution series of the polypeptide fusions with or without addition of 200 nM anti-mouse TfR antibody in 100 μL RPMI/10% FCS for 1.5 h on ice. After 2 washes with RPMI/10% FCS, cells are incubated with goat-anti-human IgG coupled to Phycoerythrin (Jackson Immunoresearch) at a dilution of 1:600 in RPMI/19% FCS for 1.5 h on ice. Cells are again washed, resuspended in RPMI/10% FCS and Phycoerythrin fluorescence measured on a FACS-Array instrument (Becton-Dickinson).

Example 4

Surface Plasmon Resonance-Based Binding Assay for Human TfR-Antibody Interaction The binding experiment were carried out on a BIAcore B 4000 (GE Healthcare) equipped with C1 sensor chip (GE Healthcare, cat.no. BR1005-35) pre-treated with anti-human Fab antibody (GE Healthcare, cat.no 28-9583-25) using a standard amine coupling chemistry procedure accordingly to the vendor's manual.

For kinetic measurements the sample antibody was immobilized applying a contact time of 60 seconds and a flow rate of 10 μL/min in phosphate buffer saline pH 7.4, 0.05% Tween 20 at 25° C. Recombinant His6-tagged human transferrin receptor (R&D systems, cat.no 2474-TR-050) was applied in increasing concentrations and the signal monitored over the time. An average time span of 150 seconds of association time and 600 seconds of dissociation time at 30 μL/min flow rate was recorded. Data were fit using a 1:1 binding model (Langmuir isotherm).

Example 5

Staining of Native Human β-Amyloid Plaques from Brain Sections of an Alzheimer's Disease Patient by Indirect Immunofluorescence Using a Bispecific Antibody as Reported Herein The bispecific antibodies can be tested for the ability to stain native human B-amyloid plaques by immunohistochemistry analysis using indirect immunofluorescence. Specific and sensitive staining of genuine human β-amyloid plaques can be demonstrated. Cryostat sections of unfixed tissue from the temporal cortex obtained postmortem from patients positively diagnosed for Alzheimer's disease are labeled by indirect immunofluorescence. A two-step incubation is used to detect bound bispecific antibody, which is revealed by affinity-purified goat anti-human (GAH555) IgG (H+L) conjugated to Alexa 555 dye (Molecular Probes). Controls can include unrelated human IgG1 antibodies (Sigma) and the secondary antibody alone, which all should give negative results.

Example 6

In Vivo β-Amyloid Plaque Decoration by a Bispecific Antibody as Reported Herein in a Mouse Model of Alzheimer's Disease Bispecific antibody can be tested in APP/PS2 double transgenic mice, a mouse model for AD-related amyloidosis (Richards, J. Neuroscience, 23 (2003) 8989-9003) for their ability to immuno-decorate B-amyloid plaques in vivo. This enabled assessment of the extent of brain penetration and binding to amyloid-β plaques. The fusion polypeptide can be administered at different doses compared to naked anti-AB monoclonal antibody and after 6 days animals are perfused with phosphate-buffered saline and the brains frozen on dry ice and prepared for cryosectioning.

The presence of the antibodies bound to β-amyloid plaques can be assessed using unfixed cryostat sections either by single-labeled indirect immunofluorescence with goat anti-human IgG (H+L) conjugated to Alexa555 dye (GAH555) (Molecular Probes) at a concentration of 15 μg/ml for 1 hour at room temperature. A counterstaining for amyloid plaques can be done by incubation with BAP-2, a mouse monoclonal antibody against Aß conjugated to Alexa 488 at a concentration of 0.5 μg/ml for 1 hour at room temperature. Slides are embedded with fluorescence mounting medium (S3023 Dako) and imaging is done by confocal laser microscopy.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A bispecific antibody comprising:
a) a full length antibody, wherein the full length antibody comprises a first full length antibody light chain and a first full length antibody heavy chain, and a second full length antibody light chain and a second full length antibody heavy chain, wherein the first full length antibody heavy chain and the first full length antibody light chain form a binding site that specifically binds to a first antigen, wherein the second full length antibody heavy chain and the second full length antibody light chain form a binding site that specifically binds to the first antigen; and
b) a Fab fragment, wherein the Fab fragment comprises a Fab heavy chain and a Fab light chain having a domain crossover such that the constant light chain domain (CL) and the constant heavy chain domain 1 (CH1) are replaced by each other, wherein the Fab heavy chain is fused to the C-terminus of the second full length antibody heavy chain to form a polypeptide, wherein the Fab heavy chain and the Fab light chain form a binding site that specifically binds to a second antigen;
wherein the first antigen is human A-beta protein, and the second antigen is human transferrin receptor; and
wherein the first full length antibody light chain and the second full length antibody light chain each comprises the amino acid sequence of SEQ ID NO: 01, the first full length antibody heavy chain comprises the amino acid sequence of SEQ ID NO: 02, the Fab light chain comprises the amino acid sequence of SEQ ID NO: 03, and the polypeptide comprising the Fab heavy chain fused to the second full length antibody heavy chain comprises the amino acid sequence of SEQ ID NO: 10.

2. A pharmaceutical formulation, comprising the bispecific antibody of claim 1 and a pharmaceutically acceptable carrier.

* * * * *

```
                          SEQUENCE LISTING

Sequence total quantity: 22
SEQ ID NO: 1            moltype = AA  length = 215
FEATURE                 Location/Qualifiers
REGION                  1..215
                        note = 0015-LC1
source                  1..215
                        mol_type = protein
                        organism = synthetic construct
SEQUENCE: 1
DIVLTQSPAT LSLSPGERAT LSCRASQSVS SSYLAWYQQK PGQAPRLLIY GASSRATGVP    60
ARFSGSGSGT DFTLTISSLE PEDFATYYCL QIYNMPITFG QGTKVEIKRT VAAPSVFIFP   120
PSDRKLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 2            moltype = AA  length = 455
FEATURE                 Location/Qualifiers
REGION                  1..455
                        note = 0015-HC1
source                  1..455
                        mol_type = protein
                        organism = synthetic construct
SEQUENCE: 2
QVELVESGGG LVQPGGSLRL SCAASGFTFS SYAMSWVRQA PGKGLEWVSA INASGTRTYY    60
ADSVKGRFTI SRDNSKNTLY LQMNSLRAED TAVYYCARGK GNTHKPYGYV RYFDVWGQGT   120
LVTVSSASTK GPSVFPLAPS SKSTSGGTAA LGCLVEDYFP EPVTVSWNSG ALTSGVHTFP   180
AVLQSSGLYS LSSVVTVPSS SLGTQTYICN VNHKPSNTKV DEKVEPKSCD KTHTCPPCPA   240
PELLGGPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPAP IEKTISKAKG QPREPQVCTL   360
PPSRDELTKN QVSLSCAVKG FYPSDIAVEW ESNGQPENNY KTTPPVLDSD GSFFLVSKLT   420
VDKSRWQQGN VFSCSVMHEA LHNHYTQKSL SLSPG                             455

SEQ ID NO: 3            moltype = AA  length = 215
FEATURE                 Location/Qualifiers
REGION                  1..215
                        note = 0015-LC2
source                  1..215
                        mol_type = protein
                        organism = synthetic construct
SEQUENCE: 3
AIQLTQSPSS LSASVGDRVT ITCRASQSIS SYLAWYQQKP GKAPKLLIYR ASTLASGVPS    60
RFSGSGSGTD FTLTISSLQP EDFATYYCQQ NYASSNVDNT FGGGTKVEIK SSASTKGPSV   120
FPLAPSSKST SGGTAALGCL VKDYFPEPVT VSWNSGALTS GVHTFPAVLQ SSGLYSLSSV   180
VTVPSSSLGT QTYICNVNHK PSNTKVDKKV EPKSC                             215

SEQ ID NO: 4            moltype = AA  length = 229
FEATURE                 Location/Qualifiers
REGION                  1..229
                        note = 0015-Fab
source                  1..229
                        mol_type = protein
                        organism = synthetic construct
SEQUENCE: 4
QSMQESGPGL VKPSQTLSLT CTVSGFSLSS YAMSWIRQHP GKGLEWIGYI WSGGSTDYAS    60
WAKSRVTISK TSTTVSLKLS SVTAADTAVY YCARRYGTSY PDYGDASGFD PWGQGTLVTV   120
SSASVAAPSV FIFPPSDEQL KSGTASVVCL LNNFYPREAK VQWKVDNALQ SGNSQESVTE   180
QDSKDSTYSL SSTLTLSKAD YEKHKVYACE VTHQGLSSPV TKSFNRGEC               229

SEQ ID NO: 5            moltype = AA  length = 42
FEATURE                 Location/Qualifiers
source                  1..42
                        mol_type = protein
                        organism = Homo sapiens
SEQUENCE: 5
DAEFRHDSGY EVHHQKLVFF AEDVGSNKGA IIGLMVGGVV IA                       42
```

```
SEQ ID NO: 6              moltype = AA  length = 215
FEATURE                   Location/Qualifiers
REGION                    1..215
                          note = 0012-LC1
source                    1..215
                          mol_type = protein
                          organism = synthetic construct
SEQUENCE: 6
DIVLTQSPAT LSLSPGERAT LSCRASQSVS SSYLAWYQQK PGQAPRLLIY GASSRATGVP    60
ARFSGSGSGT DFTLTISSLE PEDFATYYCL QIYNMPITFG QGTKVEIKRT VAAPSVFIFP   120
PSDRKLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 7              moltype = AA  length = 455
FEATURE                   Location/Qualifiers
REGION                    1..455
                          note = 0012-HC1
source                    1..455
                          mol_type = protein
                          organism = synthetic construct
SEQUENCE: 7
QVELVESGGG LVQPGGSLRL SCAASGFTFS SYAMSWVRQA PGKGLEWVSA INASGTRTYY    60
ADSVKGRFTI SRDNSKNTLY LQMNSLRAED TAVYYCARGK GNTHKPYGYV RYFDVWGQGT   120
LVTVSSASTK GPSVFPLAPS SKSTSGGTAA LGCLVEDYFP EPVTVSWNSG ALTSGVHTFP   180
AVLQSSGLYS LSSVVTVPSS SLGTQTYICN VNHKPSNTKV DEKVEPKSCD KTHTCPPCPA   240
PELLGGPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPAP IEKTISKAKG QPREPQVCTL   360
PPSRDELTKN QVSLSCAVKG FYPSDIAVEW ESNGQPENNY KTTPPVLDSD GSFFLVSKLT   420
VDKSRWQQGN VFSCSVMHEA LHNHYTQKSL SLSPG                              455

SEQ ID NO: 8              moltype = AA  length = 229
FEATURE                   Location/Qualifiers
REGION                    1..229
                          note = 0012-LC2
source                    1..229
                          mol_type = protein
                          organism = synthetic construct
SEQUENCE: 8
QSMQESGPGL VKPSQTLSLT CTVSGFSLSS YAMSWIRQHP GKGLEWIGYI WSGGSTDYAS    60
WAKSRVTISK TSTTVSLKLS SVTAADTAVY YCARRYGTSY PDYGDASGFD PWGQGTLVTV   120
SSASVAAPSV FIFPPSDEQL KSGTASVVCL LNNFYPREAK VQWKVDNALQ SGNSQESVTE   180
QDSKDSTYSL SSTLTLSKAD YEKHKVYACE VTHQGLSSPV TKSFNRGEC               229

SEQ ID NO: 9              moltype = AA  length = 688
FEATURE                   Location/Qualifiers
REGION                    1..688
                          note = 0012-HC2
source                    1..688
                          mol_type = protein
                          organism = synthetic construct
SEQUENCE: 9
QVELVESGGG LVQPGGSLRL SCAASGFTFS SYAMSWVRQA PGKGLEWVSA INASGTRTYY    60
ADSVKGRFTI SRDNSKNTLY LQMNSLRAED TAVYYCARGK GNTHKPYGYV RYFDVWGQGT   120
LVTVSSASTK GPSVFPLAPS SKSTSGGTAA LGCLVEDYFP EPVTVSWNSG ALTSGVHTFP   180
AVLQSSGLYS LSSVVTVPSS SLGTQTYICN VNHKPSNTKV DEKVEPKSCD KTHTCPPCPA   240
PELLGGPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPAP IEKTISKAKG QPREPQVYTL   360
PPCRDELTKN QVSLWCLVKG FYPSDIAVEW ESNGQPENNY KTTPPVLDSD GSFFLYSKLT   420
VDKSRWQQGN VFSCSVMHEA LHNHYTQKSL SLSPGGGSGG GGSGGGGSGG GGSAIQLTQS   480
PSSLSASVGD RVTITCRASQ SISSYLAWYQ QKPGKAPKLL IYRASTLASG VPSRFSGSGS   540
GTDFTLTISS LQPEDFATYY CQQNYASSNV DNTFGGGTKV EIKSSASTKG PSVFPLAPSS   600
KSTSGGTAAL GCLVKDYFPE PVTVSWNSGA LTSGVHTFPA VLQSSGLYSL SSVVTVPSSS   660
LGTQTYICNV NHKPSNTKVD KKVEPKSC                                      688

SEQ ID NO: 10             moltype = AA  length = 702
FEATURE                   Location/Qualifiers
REGION                    1..702
                          note = 0015-HC2
source                    1..702
                          mol_type = protein
                          organism = synthetic construct
SEQUENCE: 10
QVELVESGGG LVQPGGSLRL SCAASGFTFS SYAMSWVRQA PGKGLEWVSA INASGTRTYY    60
ADSVKGRFTI SRDNSKNTLY LQMNSLRAED TAVYYCARGK GNTHKPYGYV RYFDVWGQGT   120
LVTVSSASTK GPSVFPLAPS SKSTSGGTAA LGCLVEDYFP EPVTVSWNSG ALTSGVHTFP   180
AVLQSSGLYS LSSVVTVPSS SLGTQTYICN VNHKPSNTKV DEKVEPKSCD KTHTCPPCPA   240
PELLGGPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPAP IEKTISKAKG QPREPQVYTL   360
PPCRDELTKN QVSLWCLVKG FYPSDIAVEW ESNGQPENNY KTTPPVLDSD GSFFLYSKLT   420
```

```
VDKSRWQQGN VFSCSVMHEA LHNHYTQKSL SLSPGGGSGG GGSGGGGSGG GGSQSMQESG  480
PGLVKPSQTL SLTCTVSGFS LSSYAMSWIR QHPGKGLEWI GYIWSGGSTD YASWAKSRVT  540
ISKTSTTVSL KLSSVTAADT AVYYCARRYG TSYPDYGDAS GFDPWGQGTL VTVSSASVAA  600
PSVFIFPPSD EQLKSGTASV VCLLNNFYPR EAKVQWKVDN ALQSGNSQES VTEQDSKDST  660
YSLSSTLTLS KADYEKHKVY ACEVTHQGLS SPVTKSFNRG EC                    702

SEQ ID NO: 11            moltype = AA   length = 215
FEATURE                  Location/Qualifiers
REGION                   1..215
                         note = 0020-LC1
source                   1..215
                         mol_type = protein
                         organism = synthetic construct
SEQUENCE: 11
DIVLTQSPAT LSLSPGERAT LSCRASQSVS SSYLAWYQQK PGQAPRLLIY GASSRATGVP  60
ARFSGSGSGT DFTLTISSLE PEDFATYYCL QIYNMPITFG QGTKVEIKRT VAAPSVFIFP  120
PSDRKLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 12            moltype = AA   length = 457
FEATURE                  Location/Qualifiers
REGION                   1..457
                         note = 0020-HC1
source                   1..457
                         mol_type = protein
                         organism = synthetic construct
SEQUENCE: 12
QVELVESGGG LVQPGGSLRL SCAASGFTFS SYAMSWVRQA PGKGLEWVSA INASGTRTYY  60
ADSVKGRFTI SRDNSKNTLY LQMNSLRAED TAVYYCARGK GNTHKPYGYV RYFDVWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DEKVEPKSCD KTHTCPPCPA  240
PELLGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVCTL  360
PPSRDELTKN QVSLSCAVKG FYPSDIAVEW ESNGQPENNY KTTPPVLDSD GSFFLVSKLT  420
VDKSRWQQGN VFSCSVMHEA LHNHYTQKSL SLSPGKG                          457

SEQ ID NO: 13            moltype = AA   length = 947
FEATURE                  Location/Qualifiers
REGION                   1..947
                         note = 0020-HC2
source                   1..947
                         mol_type = protein
                         organism = synthetic construct
SEQUENCE: 13
QVELVESGGG LVQPGGSLRL SCAASGFTFS SYAMSWVRQA PGKGLEWVSA INASGTRTYY  60
ADSVKGRFTI SRDNSKNTLY LQMNSLRAED TAVYYCARGK GNTHKPYGYV RYFDVWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DEKVEPKSCD KTHTCPPCPA  240
PELLGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPCRDELTKN QVSLWCLVKG FYPSDIAVEW ESNGQPENNY KTTPPVLDSD GSFFLYSKLT  420
VDKSRWQQGN VFSCSVMHEA LHNHYTQKSL SLSPGGGSGG GGSGGGGSGG GGSAIQLTQS  480
PSSLSASVGD RVTITCRASQ SISSYLAWYQ QKPGKAPKLL IYRASTLASG VPSRFSGSGS  540
GTDFTLTISS LQPEDFATYY CQQNYASSNV DNTFGGGTKV EIKRTVAAPS VFIFPPSDEQ  600
LKSGTASVVC LLNNFYPREA KVQWKVDNAL QSGNSQESVT EQDSKDSTYS LSSTLTLSKA  660
DYEKHKVYAC EVTHQGLSSP VTKSFNRGEC GGGGSGGGGS GGGGSGGGGS GGGGSGGGGS  720
GGQSMQESGP GLVKPSQTLS LTCTVSGFSL SSYAMSWIRQ HPGKGLEWIG YIWSGGSTDY  780
ASWAKSRVTI SKTSTTVSLK LSSVTAADTA VYYCARRYGT SYPDYGDASG FDPWGQGTLV  840
TVSSASTKGP SVFPLAPSSK STSGGTAALG CLVKDYFPEP VTVSWNSGAL TSGVHTFPAV  900
LQSSGLYSLS SVVTVPSSSL GTQTYICNVN HKPSNTKVDK KVEPKSC                947

SEQ ID NO: 14            moltype = AA   length = 215
FEATURE                  Location/Qualifiers
REGION                   1..215
                         note = 0024-LC1
source                   1..215
                         mol_type = protein
                         organism = synthetic construct
SEQUENCE: 14
DIVLTQSPAT LSLSPGERAT LSCRASQSVS SSYLAWYQQK PGQAPRLLIY GASSRATGVP  60
ARFSGSGSGT DFTLTISSLE PEDFATYYCL QIYNMPITFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 15            moltype = AA   length = 455
FEATURE                  Location/Qualifiers
REGION                   1..455
                         note = 0024-HC1
source                   1..455
```

```
                            mol_type = protein
                            organism = synthetic construct
SEQUENCE: 15
QVELVESGGG LVQPGGSLRL SCAASGFTFS SYAMSWVRQA PGKGLEWVSA INASGTRTYY    60
ADSVKGRFTI SRDNSKNTLY LQMNSLRAED TAVYYCARGK GNTHKPYGYV RYFDVWGQGT   120
LVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKKVEPKSCD KTHTCPPCPA   240
PELLGGPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPAP IEKTISKAKG QPREPQVCTL   360
PPSRDELTKN QVSLSCAVKG FYPSDIAVEW ESNGQPENNY KTTPPVLDSD GSFFLVSKLT   420
VDKSRWQQGN VFSCSVMHEA LHNHYTQKSL SLSPG                              455

SEQ ID NO: 16               moltype = AA  length = 215
FEATURE                     Location/Qualifiers
REGION                      1..215
                            note = 0024-LC2
source                      1..215
                            mol_type = protein
                            organism = synthetic construct
SEQUENCE: 16
AIQLTQSPSS LSASVGDRVT ITCRASQSIS SYLAWYQQKP GKAPKLLIYR ASTLASGVPS    60
RFSGSGSGTD FTLTISSLQP EDFATYYCQQ NYASSNVDNT FGGGTKVEIK SSASTKGPSV   120
FPLAPSSKST SGGTAALGCL VKDYFPEPVT VSWNSGALTS GVHTFPAVLQ SSGLYSLSSV   180
VTVPSSSLGT QTYICNVNHK PSNTKVDKKV EPKSC                              215

SEQ ID NO: 17               moltype = AA  length = 702
FEATURE                     Location/Qualifiers
REGION                      1..702
                            note = 0024-HC2
source                      1..702
                            mol_type = protein
                            organism = synthetic construct
SEQUENCE: 17
QVELVESGGG LVQPGGSLRL SCAASGFTFS SYAMSWVRQA PGKGLEWVSA INASGTRTYY    60
ADSVKGRFTI SRDNSKNTLY LQMNSLRAED TAVYYCARGK GNTHKPYGYV RYFDVWGQGT   120
LVTVSSASTK GPSVFPLAPS SKSTSGGTAA LGCLVKDYFP EPVTVSWNSG ALTSGVHTFP   180
AVLQSSGLYS LSSVVTVPSS SLGTQTYICN VNHKPSNTKV DKKVEPKSCD KTHTCPPCPA   240
PELLGGPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPAP IEKTISKAKG QPREPQVYTL   360
PPCRDELTKN QVSLWCLVKG FYPSDIAVEW ESNGQPENNY KTTPPVLDSD GSFFLYSKLT   420
VDKSRWQQGN VFSCSVMHEA LHNHYTQKSL SLSPGGGSGG GGSGGGGSGG GGSQSMQESG   480
PGLVKPSQTL SLTCTVSGFS LSSYAMSWIR QHPGKGLEWI GYIWSGGSTD YASWAKSRVT   540
ISKTSTTVSL KLSSVTAADT AVYYCARRYG TSYPDYGDAS GFDPWGQGTL VTVSSASVAA   600
PSVFIFPPSD EQLKSGTASV VCLLNNFYPR EAKVQWKVDN ALQSGNSQES VTEQDSKDST   660
YSLSSTLTLS KADYEKHKVY ACEVTHQGLS SPVTKSFNRG EC                      702

SEQ ID NO: 18               moltype = AA  length = 126
FEATURE                     Location/Qualifiers
source                      1..126
                            mol_type = protein
                            organism = Homo sapiens
SEQUENCE: 18
QVELVESGGG LVQPGGSLRL SCAASGFTFS SYAMSWVRQA PGKGLEWVSA INASGTRTYY    60
ADSVKGRFTI SRDNSKNTLY LQMNSLRAED TAVYYCARGK GNTHKPYGYV RYFDVWGQGT   120
LVTVSS                                                              126

SEQ ID NO: 19               moltype = AA  length = 108
FEATURE                     Location/Qualifiers
source                      1..108
                            mol_type = protein
                            organism = Homo sapiens
SEQUENCE: 19
DIVLTQSPAT LSLSPGERAT LSCRASQSVS SSYLAWYQQK PGQAPRLLIY GASSRATGVP    60
ARFSGSGSGT DFTLTISSLE PEDFATYYCL QIYNMPITFG QGTKVEIK                108

SEQ ID NO: 20               moltype = AA  length = 122
FEATURE                     Location/Qualifiers
REGION                      1..122
                            note = 299-023 VH humanization variant_DASG
source                      1..122
                            mol_type = protein
                            organism = synthetic construct
SEQUENCE: 20
QSMQESGPGL VKPSQTLSLT CTVSGFSLSS YAMSWIRQHP GKGLEWIGYI WSGGSTDYAS    60
WAKSRVTISK TSTTVSLKLS SVTAADTAVY YCARRYGTSY PDYGDASGFD PWGQGTLVTV   120
SS                                                                  122

SEQ ID NO: 21               moltype = AA  length = 110
FEATURE                     Location/Qualifiers
```

```
REGION                  1..110
                        note = 299-009 VL humanization variant_NYA
source                  1..110
                        mol_type = protein
                        organism = synthetic construct
SEQUENCE: 21
AIQLTQSPSS LSASVGDRVT ITCRASQSIS SYLAWYQQKP GKAPKLLIYR ASTLASGVPS     60
RFSGSGSGTD FTLTISSLQP EDFATYYCQQ NYASSNVDNT FGGGTKVEIK               110

SEQ ID NO: 22           moltype = AA   length = 760
FEATURE                 Location/Qualifiers
source                  1..760
                        mol_type = protein
                        organism = Homo sapiens
SEQUENCE: 22
MMDQARSAFS NLFGGEPLSY TRFSLARQVD GDNSHVEMKL AVDEEENADN NTKANVTKPK     60
RCSGSICYGT IAVIVFFLIG FMIGYLGYCK GVEPKTECER LAGTESPVRE EPGEDFPAAR    120
RLYWDDLKRK LSEKLDSTDF TGTIKLLNEN SYVPREAGSQ KDENLALYVE NQFREFKLSK    180
VWRDQHFVKI QVKDSAQNSV IIVDKNGRLV YLVENPGGYV AYSKAATVTG KLVHANFGTK    240
KDFEDLYTPV NGSIVIVRAG KITFAEKVAN AESLNAIGVL IYMDQTKFPI VNAELSFFGH    300
AHLGTGDPYT PGFPSPSFNHTQ FPPSRSSGLP NIPVQTISRA AAEKLFGNME GDCPSDWKTD  360
STCRMVTSES KNVKLTVSNV LKEIKILNIF GVIKGFVEPD HYVVVGAQRD AWGPGAAKSG    420
VGTALLLKLA QMFSDMVLKD GFQPSRSIIF ASWSAGDFGS VGATEWLEGY LSSLHLKAFT    480
YINLDKAVLG TSNFKVSASP LLYTLIEKTM QNVKHPVTGQ FLYQDSNWAS KVEKLTLDNA    540
APPFLAYSGI PAVSFCFCED TDYPYLGTTM DTYKELIERI PELNKVARAA AEVAGQFVIK    600
LTHDVELNLD YERYNSQLLS FVRDLNQYRA DIKEMGLSLQ WLYSARGDFF RATSRLTTDF    660
GNAEKTDRFV MKKLNDRVMR VEYHFLSPYV SPKESPFRHV FWGSGSHTLP ALLENLKLRK    720
QNNGAFNETL FRNQLALATW TIQGAANALS GDVWDIDNEF                         760
```